(12) United States Patent
Ye et al.

(10) Patent No.: US 7,629,135 B2
(45) Date of Patent: Dec. 8, 2009

(54) TOLL-LIKE RECEPTOR AGONISTS AND ANTAGONISTS AND METHODS OF USE THEREOF

(75) Inventors: Richard D. Ye, Westmont, IL (US); Ni Cheng, Chicago, IL (US); Rong L. He, Chicago, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 11/963,610

(22) Filed: Dec. 21, 2007

(65) Prior Publication Data

US 2008/0167242 A1 Jul. 10, 2008

Related U.S. Application Data

(60) Provisional application No. 60/876,699, filed on Dec. 22, 2006.

(51) Int. Cl.
| | |
|---|---|
| G01N 33/53 | (2006.01) |
| G01N 33/567 | (2006.01) |
| C12N 5/00 | (2006.01) |
| C12N 5/02 | (2006.01) |
| C12P 21/06 | (2006.01) |
| C07K 14/00 | (2006.01) |
| A61K 38/29 | (2006.01) |
| C07H 21/04 | (2006.01) |
| C07H 21/02 | (2006.01) |

(52) U.S. Cl. .................. 435/7.2; 435/7.1; 435/325; 435/375; 435/69.1; 530/350; 530/300; 530/351; 530/399; 536/23.4; 536/23.5

(58) Field of Classification Search .................. None
See application file for complete search history.

(56) References Cited

U.S. PATENT DOCUMENTS

| | | |
|---|---|---|
| 2005/0004144 A1 | 1/2005 | Carson et al. |
| 2005/0113345 A1* | 5/2005 | Chow et al. .................. 514/114 |
| 2005/0119273 A1 | 6/2005 | Lipford et al. |
| 2005/0163764 A1 | 7/2005 | Medzhitov et al. |
| 2005/0208470 A1* | 9/2005 | Latz et al. .................. 435/4 |
| 2006/0147427 A1 | 7/2006 | Penninger et al. |
| 2006/0153844 A1 | 7/2006 | Kundig et al. |
| 2006/0179499 A1 | 8/2006 | Tirabassi et al. |
| 2006/0229233 A1 | 10/2006 | Frenkel et al. |

FOREIGN PATENT DOCUMENTS

| | | |
|---|---|---|
| WO | WO-2004/093778 | 11/2004 |
| WO | WO-2005/102040 | 11/2005 |
| WO | WO-2006/071583 | 7/2006 |
| WO | WO-2007/053428 | 5/2007 |
| WO | WO-2007/053455 | 5/2007 |

OTHER PUBLICATIONS

Papadimitraki et al 2007. Jnl of Autoimmunity. 29:310-318.*
Uhlar et al 1999. Eur J. Biochem. 265:501-523.*
Hamilton. 2008. Nature Reviews, Immunology. 8:533-544.*
Migita et al (2004. FEBS Letters 569:235-239.*
Hiratsuka et al 2008. Nature Cell Biology 10:1349-1355.*
He et al., Serum amyloid a is an endogenous ligand that differentially induces IL-12 and IL-23. *J. Immunol.* 177: 4072-4079 (2006).
LeBouder et al., Soluble forms of toll-like receptor (TLR)2 capable of modulating TLR2 signaling are present in human plasma and breast milk. *J. Immunol.* 171: 6680-9 (2003).
Meng et al., Antagonistic antibody prevents toll-like receptor 2-driven lethal shock-like syndromes. *J. Clin. Invest.* 113:1473-81 (2004).
Rutz et al., Toll-like receptor 9 binds single-stranded CpG-DNA in a sequence- and pH-dependent manner. *Eur. J. Immunol.* 34: 2541-50 (2004).
Wyllie et al., Evidence for an accessory protein function for Toll-like receptor 1 in antibacterial responses. *J. Immunol.* 165: 7125-32 (2000).
Yang et al., Toll-like receptor-2 mediates lipopolysaccharide-induced cellular signaling, *Nature.* 395: 284-8 (1998).

\* cited by examiner

*Primary Examiner*—Manjunath N Rao
*Assistant Examiner*—Shulamith H Shafer
(74) *Attorney, Agent, or Firm*—Marshall, Gerstein & Borun LLP

(57) ABSTRACT

The present disclosure relates to compositions and methods of modulating inflammatory and immune responses through binding of SAA to TLR2 in a subject (e.g., human, non-human primate, rodent, etc.), and compositions and methods for screening TLR2 agonists and antagonists. In the studies described herein, a potential role of SAA in neutrophilia was investigated and the results demonstrated that SAA is a potent inducer for macrophage secretion of G-CSF, which leads to neutrophilia in mice. Using G-CSF$^{-/-}$ and TLR2$^{-/-}$ mice, it was found that the SAA-induced neutrophilia is dependent on TLR2-mediated production of G-CSF. Based on direct binding assay and gain-of-function studies in TLR2-transfected cells, SAA was identified as a novel ligand for TLR2 and a link between increased SAA concentration and TLR2-mediated inflammatory responses such as neutrophilia was established. Additional embodiments are disclosed.

16 Claims, 14 Drawing Sheets

A

B

5x NF-kB binding sequence: (TGGGGACTTTCCGC)$_5$

Expression of selected cytokine genes in SAA-stimulated mouse macrophages from wild type and TLR2 knockout mice.

| Index | Symbol | Gene Description | Fold induction | | TLR2-/-/Wt Ratio (%) |
|---|---|---|---|---|---|
| | | | Wild Type | TLR2-/- | |
| 1 | CSF1 | Colony stimulating factor 1 (macrophage) | 11.17 ± 0.49 | 1.76 ± 0.05 | 16.06 ± 0.52 |
| 2 | CSF3 | Colony stimulating factor 3 (granulocyte) | 13.24 ± 0.41 | 3.73 ± 0.14 | 29.06 ± 1.15 |
| 3 | IL1f6 | Interleukin 1 family, member 6 | 14.91 ± 4.85 | 3.45 ± 1.12 | 20.53 ± 6.67 |
| 4 | IL1rn | Interleukin 1 receptor antagonist | 2.73 ± 0.14 | 0.52 ± 0.06 | 19.52 ± 2.48 |
| 5 | IL10 | Interleukin 10 | 2.15 ± 0.08 | 0.95 ± 0.05 | 36.32 ± 1.82 |
| 6 | IL12α | Interleukin 12, subunit p35 | 2.55 ± 0.13 | 1.61 ± 0.13 | 66.67 ± 5.64 |
| 7 | IL12β | Interleukin 12, subunit p40 | 32.81 ± 4.50 | 4.46 ± 0.14 | 14.18 ± 0.47 |
| 8 | IL18 | Interleukin 18 | 2.82 ± 0.24 | 1.01 ± 0.05 | 43.91 ± 2.70 |
| 9 | IL19 | Interleukin 19 | 117.01 ± 33.62 | 8.41 ± 3.00 | 7.33 ± 2.61 |
| 10 | LTB | Lymphotoxin B | 1.83 ± 0.03 | 0.83 ± 0.17 | 45.2 ± 9.52 |
| 11 | TNFSF10 | Tumor necrosis factor superfamily, member 10 | 3.39 ± 1.11 | 1.46 ± 0.30 | 34.65 ± 7.20 |
| 12 | TNFSF15 | Tumor necrosis factor superfamily, member 15 | 23.89 ± 2.51 | 6.80 ± 0.94 | 30.74 ± 4.27 |

FIG. 14

TOLL-LIKE RECEPTOR AGONISTS AND ANTAGONISTS AND METHODS OF USE THEREOF

PRIOR APPLICATION

The present application claims the priority of U.S. provisional patent application No. 60/876,699 filed Dec. 22, 2006, by Richard D. Ye et al., entitled "IDENTIFICATION OF SERUM AMYLOID A AS AN ENDOGENOUS LIGAND FOR TOLL-LIKE RECEPTOR 2." All sections of the aforementioned application are incorporated herein by reference.

STATEMENT AS TO FEDERALLY SPONSORED RESEARCH

This invention was made with government support under AI 040176 awarded by the National Institutes of Health/National Institute of Allergy and Infectious Diseases. The government has certain rights in this invention.

FIELD OF THE DISCLOSURE

The present disclosure relates generally to the fields of molecular biology, genetics, and immunology, and more specifically to compositions and methods for modulating Toll-like receptor 2 (TLR2) activity, inflammation, and immune responses in a mammal (e.g., a human, non-human primate, rodent, etc.) by serum amyloid A (SAA).

BACKGROUND

Increased neutrophil count in peripheral blood, known as neutrophilia, often results from bacterial infection. Since neutrophils possess highly specialized bactericidal functions such as degranulation and superoxide production, an increase in the number of available neutrophils is beneficial to host defense and can facilitate the elimination of invading bacteria. Neutrophilia also results from noninfectious insults including trauma, malignancy, surgery and certain autoimmune diseases. Neutrophilia is one of the clinical signs of systemic inflammatory response syndrome, which often lacks a proven source of infection (Robertson and Coopersmith, 2006). An increase in the number of neutrophils can facilitate their tissue infiltration, contributing to tissue damage as seen in sterile inflammation and autoimmune diseases such as rheumatoid arthritis. Whereas the mechanisms by which bacterial infection causes neutrophilia have been clearly defined, the endogenous factors and pathways responsible for neutrophilia under noninfectious conditions remain to be characterized.

In response to inflammatory stimuli, neutrophils move from storage pools into blood circulation. This initial process is followed by mobilization of bone marrow reserves and expansion of pluoripotent marrow cells committed to granulocytic differentiation, which requires granulocyte colony-stimulating factor (G-CSF), a potent cytokine and hematopoietic growth factor (Demetri and Griffin, 1991). In resting state, the serum concentration of G-CSF is <40 pg/ml in healthy individuals. It increases by up to several hundred folds during acute infection and sepsis (Hareng and Hartung, 2002). G-CSF concentration also increases in response to noninfectious insults such as trauma, malignancy and surgery, collectively known as the acute-phase response (Kushner and Rzewnicki, 1999). The association between neutrophilia and increased serum G-CSF level has been well documented. All leukocytes express G-CSF when challenged with exogenous stimuli such as LPS, LTA, phorbo 12-myristate 13-acetate (PMA), phytohaemagglutinin (PHA), endogenous cytokines and hematopoietic growth factors such as TNFα, IL-1β, IL-3, IL-17, GM-CSF and M-CSF (Demetri and Griffin, 1991; Hareng and Hartung, 2002). However, a causal relationship between increased acute-phase proteins, enhanced production of G-CSF and neutrophilia has not been established.

SAA is a major acute-phase protein of 104 amino acids whose concentration in plasma increases by up to 1.000-fold during acute-phase response (to trauma, infection and tissue injury) (Gabay and Kushner, 1999). A correlation between elevated SAA concentration and progression of inflammatory diseases such as arthritis, inflammatory bowel diseases and atherosclerosis has been reported (Chambers et al., 1983; Fyfe et al., 1997; Ma11e and De Beer, 1996). Despite the wide use of these biomarkers, the biological functions of SAA and CRP were not known until recently. Several published reports demonstrate that SAA has cytokine-like activity and can stimulate production of other cytokines by monocytes and macrophages (Furlaneto and Campa, 2000; Patel et al., 1998; Vallon et al., 2001). Studies have shown that SAA can induce the expression of proinflammatory cytokines such as IL-1β, TNFα, and IL-6, growth-stimulatory cytokines such as G-CSF, chemokines such as IL-8 and MCP-1, and immunomodulatory cytokines such as WL-12p40 and IL-23 (He et al., 2003; He et al., 2006). The known SAA receptors and binding partners are formyl peptide receptor-like 1 (FPRL1), scavenge receptor BI (SR-BI), Tanis, the integrin $\alpha_{IIb}\beta_3$, and heparin and heparan sulfate. These receptors and binding partners are not specialized in the induction of proinflammatory cytokines, although activation of some (e.g. FPRL1) can lead to gene expression. Therefore the receptor(s) responsible for SAA-induced proinflammatory cytokine expression remain to be identified.

The precise mechanism by which SAA regulates inflammation, however, remains unclear. Elucidating the role of SAA in inflammation and immunity and identifying the binding partners of SAA involved in inflammation and immunity should prove useful for identifying therapeutic targets for a variety of diseases.

BRIEF DESCRIPTION OF THE DRAWINGS

FIG. 7A shows the response of a stable HeLa cell line expressing the transfected TLR2 cDNA and a 5xNF-κB luciferase reporter to SAA stimulation. Pam3CSK4 is a known agonist for TLR2 and was used as a control. TNFα was used as another control, which does not use TLR2 for signaling. FIG. 7B is time course of SAA-induced IL-8 secretion in TLR2-HeLa cells compared to mock-transfected HeLa cells. SAA was used at 1 μM and the cells were stimulated for up to 24 hours. The supernatant was collected and secreted IL-8 was measured using ELISA.

FIG. 14 is an expression of selected cytokine genes in SAA-stimulated mouse macrophages from wild type and TLR2 knockout mice.

DETAILED DESCRIPTION

Figure 1:
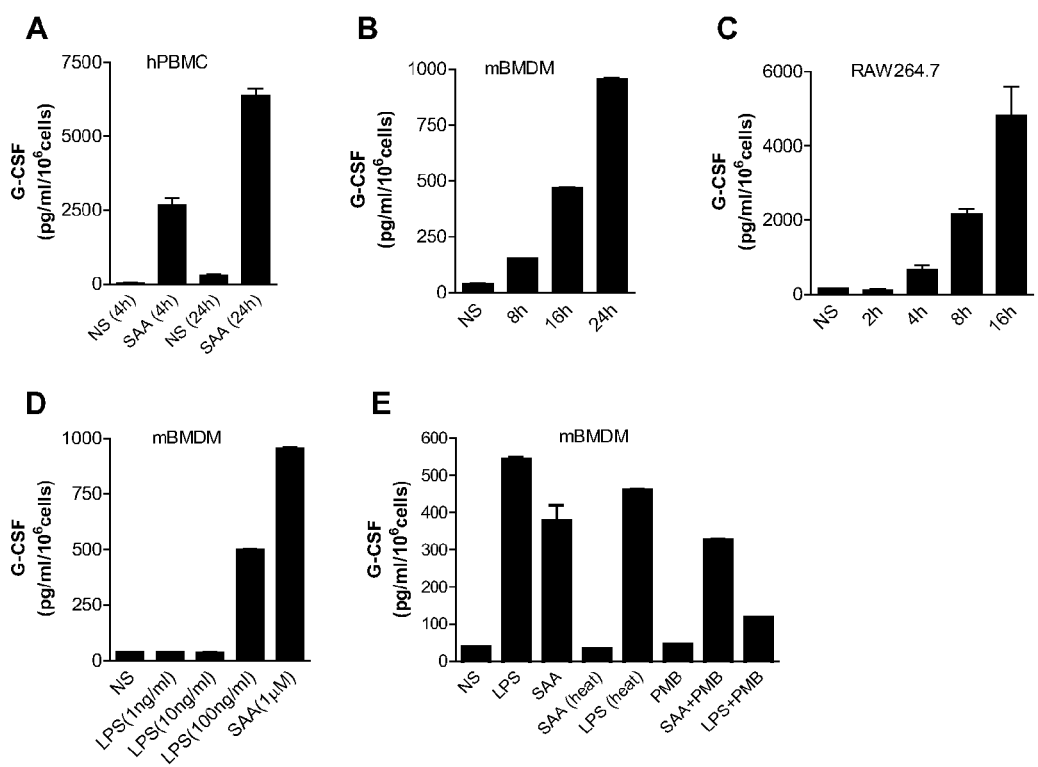
FIG. 1 is a series of graphs showing SAA induction of G-CSF secretion in monocytes and macrophages. Freshly prepared human PBMC (A), mouse BMDM (B) and mouse RAW264.7 cells (C) were stimulated with SAA (1 μM; same below) or buffer (NS), and the secreted G-CSF was determined with ELISA at the indicated time points. (D) Mouse BMDM was incubated with different concentrations of LPS from *Escherichia coli* strain 0111:B4 as indicated or with SAA for 24 h, prior to measurement of G-CSF concentration. (E) Mouse BMDM was incubated for 16 h with LPS (1 μg/ml), SAA, heat-treated LPS and SAA (100° C. for 25 min), or polymyxin B (50 μg/ml, 1 h)-pretreated SAA or LPS. The secreted G-CSF was determined using ELISA. Data shown are means ±SEM from three experiments.

The present disclosure relates to compositions and methods of modulating inflammatory and immune responses through binding of SAA to TLR2 in a subject (e.g., human, non-human primate, rodent, etc.), and compositions and methods for screening TLR2 agonists and antagonists. In the studies described herein, a potential role of SAA in neutrophilia was investigated and the results demonstrated that SAA is a potent inducer for macrophage secretion of G-CSF, which leads to neutrophilia in mice. Using G-CSF$^{-/-}$ and TLR2$^{-/-}$ mice, it was found that the SAA-induced neutrophilia is dependent on TLR2-mediated production of G-CSF. Based on direct binding assay and gain-of-function studies in TLR2-transfected cells, SAA was identified as a novel ligand for TLR2 and a link between increased SAA concentration and inflammatory responses such as neutrophilia was established.

In one embodiment of the present disclosure, a method includes providing a composition including SAA protein or a nucleic acid encoding SAA protein, and administering the composition to a subject. Administering the composition to the subject stimulates an immune response in the subject. The composition can include SAA protein that activates TLR2 in at least one cell (e.g., a plurality of cells, a tissue) in the subject resulting in expression of at least one cytokine in the subject. In one example of a method, the composition includes a nucleic acid encoding SAA protein, and SAA protein expressed by the nucleic acid activates TLR2 in at least one cell (e.g., a plurality of cells, a tissue) in the subject resulting in expression of at least one cytokine in the subject. Administering the composition to the subject (e.g., human, non-human primate, rodent, etc.) can stimulate an inflammatory response in the subject. The composition can be an adjuvant and administered to a subject (e.g., human, non-human primate, rodent) in combination with an antigen. The composition can further include a pharmaceutically acceptable carrier.

In one embodiment of the present disclosure, a method includes: providing a plurality of cells, each cell including a first purified nucleic acid encoding TLR2 and a second purified nucleic acid including a reporter gene; contacting the plurality of cells with a plurality of candidate agents; detecting expression of the reporter gene in at least one of the cells, wherein expression of the reporter gene indicates activation of TLR2; and correlating activation of TLR2 with at least one of the plurality of candidate agents. In this method, the plurality of candidate agents are screened for at least one agent able to activate TLR2. Expression of the reporter gene in at least one of the cells is compared to expression of the reporter gene in at least one control cell not contacted with the plurality of candidate agents.

In one embodiment of the present disclosure, a method includes: providing a plurality of cells, each cell including a first purified nucleic acid encoding TLR2, a second purified nucleic acid including a reporter gene, and at least one SAA protein; contacting the plurality of cells with a plurality of candidate agents; analyzing expression of the reporter gene in the plurality of the cells, wherein expression of the reporter gene indicates activation of TLR2 by the at least one SAA protein; comparing activation of TLR2 by the at least one SAA protein in at least one cell of the plurality of cells with activation of TLR2 by at least one SAA protein in at least one control cell; and correlating a decrease in activation of TLR2 by the at least one SAA protein in the at least one cell of the plurality of cells compared to activation of TLR2 by the at least one SAA protein in the at least one control cell with one agent of the plurality of agents, wherein the one agent of the plurality of agents prevents activation of TLR2 by SAA in a cell. The plurality of agents includes at least one of a small molecule, a macromolecule (e.g., antibody), a peptide, and a nonpeptide, wherein the small molecule, macromolecule (e.g., antibody), peptide, and nonpeptide can be naturally occurring or synthetic.

In one embodiment of the present disclosure, a method includes providing a composition including a TLR2 antagonist and contacting a plurality of cells with the composition, wherein the composition disrupts binding of TLR2 to SAA in the plurality of cells and modulates induction of proinflammatory cytokines in the plurality of cells. The composition can decrease induction of proinflammatory cytokines in the plurality of cells. The TLR2 antagonist is one of a small molecule, a macromolecule (e.g., antibody), a peptide, and a nonpeptide, wherein the small molecule, macromolecule (e.g., antibody), peptide, and nonpeptide can be naturally occurring or synthetic. The composition can further include a pharmaceutically acceptable carrier. The TLR2 can include a TLR2 extracellular domain (ectodomain) fused to an Fc fragment and the composition can be a component of an ELISA assay, wherein an effect of the antagonist on binding of SAA to the TLR2 extracellular domain can be determined.

In one embodiment of the present disclosure, a HeLa cell includes a first purified nucleic acid encoding TLR2 and a second purified nucleic acid including a plurality of NF-κB binding sites operably linked to at least one expression control sequence and a reporter gene. The expression control sequence can be a promoter. The reporter gene can encode luciferase.

TLRs are a class of 11 receptors (TLR1, TLR2, TLR3, TLR4, TLR5, TLR6, TLR7, TLR8, TLR9, TLR10, TLR 11) that recognize special patterns of pathogens, termed pathogen-associated molecular patterns (Medzhitov and Janeway, 2000). These receptors are expressed in innate immune cells (neutrophils, monocytes, macrophages, dendritic cells) and in other types of cells such as endothelial cells. Their ligands include bacterial products such as LPS, peptidoglycans, lipopeptides, and CpG DNA. Since their discovery in the late '90s, TLRs have been well characterized as receptors that bind to exogenous ligands and mediate innate immune responses leading to the elimination of invading microbes. The TLR-triggered signaling pathway leads to activation of transcription factors including NF-κB, which is critical for the induced expression of proinflammatory cytokines and chemokines (Akira and Sato, 2003). TLRs also interact with each other. For example, TLR2 can form functional heterodimers with TLR1 or TLR6. The TLR2/1 dimer has different ligand binding profile than the TLR2/6 dimer (Ozinsky et al., 2000). In some embodiments wherein a cell or plurality of cells includes a purified nucleic acid encoding TLR2, the cell or plurality of cells can also include a nucleic acid encoding another TLR2, such as TLR1. In such an embodiment, both TLR2 and TLR1 are expressed, and form a functional heterodimer.

The term "agonist" as used herein refers to an agent that activates cell signaling through a TLR2. An agonist can be a naturally occurring activator of TLR2, such as SAA, a ligand for TLR2. An agonist can also be a non-naturally occurring activator of TLR2.

As used herein, the term "antagonist" means an agent that inhibits the effect of an agonist. For example, a TLR2 antagonist inhibits SAA activation of TLR2. An antagonist can be a small molecule, a macromolecule (e.g., antibody), a peptide, and a nonpeptide. A small molecule, macromolecule (e.g., antibody), peptide, and nonpeptide can be naturally occurring or synthetic.

By the term "effective amount" is meant an amount of a composition as described herein that when administered to a subject, is sufficient for therapeutic efficacy (e.g., preventing or mitigating an inflammatory response).

As used herein, "immunologically effective amount," means that the administration of that amount to a subject, either in a single dose or as part of a series, is effective for treatment, e.g., stimulating an innate or adaptive immune response in a subject.

By the term "gene" is meant a nucleic acid molecule that codes for a particular protein, or in certain cases, a functional or structural RNA molecule. For example, the saa gene encodes the SAA protein. saa nucleic acids (e.g., genes) are known in the art (e.g., human saa1: accession no. CR542241; human saa2: accession no. NM 030754; and saa4: BC007026).

As used herein, a "nucleic acid," or "nucleic acid molecule," mean a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote.

As used herein, "protein" or "polypeptide" are used synonymously to mean any peptide-linked chain of amino acids, regardless of length or post-translational modification, e.g., glycoslylation or phosphorylation. By the term "SAA" is meant a protein, or a fragment thereof, encoded by any one of the SAA gene family (e.g., saa1, saa2, saa4), the expression of which can be inducible or constitutive. An example of a SAA protein is the acute-phase SAA encoded by the human saa1 and saa2 genes as described in the Examples below.

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

By the phrase "expression control sequence" is meant a nucleic acid that regulates the replication, transcription and translation of a coding sequence in a recipient cell. Examples of expression control sequences include promoter sequences, polyadenylation (pA) signals, introns, transcription termination sequences, enhancers, upstream regulatory domains, origins of replication, and internal ribosome entry sites. The term "promoter" is used herein to refer to a DNA regulatory sequence to which RNA polymerase binds, initiating transcription of a downstream (3' direction) coding sequence.

As used herein, the term "nonpeptide" means any molecule, natural or synthetic, other than a molecule consisting of two or more amino acids linked by the carboxyl group of one amino acid to the amino group of another amino acid.

Methods described herein include a composition including an agent (e.g., SAA protein or a nucleic acid encoding SAA protein) that when administered to a subject, activates a TLR and stimulates an immune response in the subject. Such an agent can activate TLR2 by, for example, interacting with TLR2 (e.g., SAA binding to TLR2) or activating any downstream cellular pathway that occurs upon binding of a ligand to a TLR. An agent that activates TLR can also enhance the availability or accessability of any endogenous or naturally occurring ligand of TLR2. An agent that activates TLR2 can alter transcription of genes, increase translation of mRNA or increase the activity of proteins that are involved in mediating TLR2 cellular processes. For example, an agent that activates TLR2 (e.g., SAA) can induce expression of IL-8, IL-12p40, and IL-23.

A composition including an agent that activates TLR2 (e.g., an agonist, SAA, a mimetic of SAA) can be administered to a subject (e.g., rodent, human, non-human primate) for stimulating an immune response in a subject in need thereof (e.g., a subject suspected of having exposure to infectious disease, a subject having cancer, etc.).

Administration of a composition including an agent that activates TLR2 to a subject can induce expression of immunomodulatory cytokines such as IL-12p40, IL-8, and IL-23. In some embodiments, a composition including an agent that activates TLR2 is an adjuvant and is administered with a specific antigen to potentiate the effect of vaccination against an infectious agent or abnormal cell such as a cancer cell. Such a composition includes an immunologically effective amount of the agent that activates TLR2.

In other methods described herein, a composition includes a TLR2 antagonist that when contacted with cells, disrupts binding of TLR2 to SAA in the cells and modulates induction of proinflammatory cytokines in the plurality of cells. In a typical embodiment, the composition decreases induction of proinflammatory cytokines in the cells. A composition including a TLR2 antagonist can be administered to a subject having inflammation at one or more sites (e.g., tissues, organs, muscles, etc.). A composition including a TLR2 antagonist can also be administered to a subject having an inflammatory disease. Examples of inflammatory diseases include arthritis, inflammatory bowel disease, and atherosclerosis. Administration of a composition including a TLR2 antagonist can suppress the induction of proinflammatory cytokines (e.g., IL-8, IL-23, TNF family of cytokines, etc.), growth-stimulatory cytokines, immunomodulatory cytokines, tissue factor, and tissue-degrading enzymes, by SAA in the subject.

In the present disclosure, cells that can be used to screen for agents that modulate TLR2 activity (e.g., activate TLR2, inhibit binding of SAA to TLR2, etc.) are encompassed. As one example, HeLa cells transfected with a purified nucleic acid (e.g., vector) encoding TLR2 (or a TLR2/TLR1 heterodimer, for example) and a purified nucleic acid (e.g., vector) including a plurality of NF-κB binding sites operably linked to an expression control sequence and a reporter gene can be used to screen for agents that modulate TLR2 activity. In the methods described below, TLR2-HeLa cells were generated by transfection of HeLa cells with the expression construct pUNO-hTLR2 (InvivoGen). Stable transfectants were selected with Blasticidin at 20 µg/ml for 2 weeks. Mock-transfected HeLa cells were generated similarly, with a pUNO empty vector. Cells were maintained in DMEM supplemented with 10% heat-inactivated FBS, 2 mM L-glutamine, 100 IU/ml penicillin, and 50 µg/ml streptomycin. This methodology can be applied to any suitable cells, however, for preparing cells that can be used to screen for agents that modulate TLR2 activity. A suitable cell is any cell that does not contain substantial levels of endogenous TLR2.

Methods of screening for agents that modulate TLR2 activity (e.g., activate TLR2, inhibit binding of SAA to TLR2, etc.) are described herein. In a first example of such a screening assay, TLR2-HeLa cells (or other suitable cells transfected with a construct encoding TLR2 or a TLR2/TLR1 heterodimer) are transfected with an NF-κB reporter gene. Although this can be done with transient transfection, a TLR2-HeLa-NF-κB reporter cell line can alternatively be used and provides convenience and consistency between experiments. This cell line is stimulated with SAA to induce NF-κB-driven luciferase reporter expression. This establishes a standard for the activation state of the receptor by SAA. As a negative control, a mock-transfected cell line (lacking TLR2 but containing the same reporter) is used (see below). Also, as a positive control, the TLR2-HeLa-NF-κB cell line is stimulated with Pam3CSK4, a known TLR2 agonist, to determine the effectiveness of TLR2-mediated NF-κB activation. In another control, HeLa cells without any manipulation are transfected with the same reporter gene (e.g., a HeLa cell line having this reporter stably expressed), and then stimulated with TNF-alpha. This control is used to evaluate TLR2-independent NF-κB activation. Typically, in the first round of screening, only the TLR2-HeLa with the NF-κB reporter (the TLR2-HeLa-NF-κB cell line) is used (ideally, the negative control cells are used for background subtraction), and these cells are stimulated with SAA in the presence of the unknown compounds which can be natural compounds or synthetic compounds in a combinatorial compound library, for example, for the screening of compounds that can modulate SAA-induced, TLR2-mediated NF-κB activation. Modulation can be positive for enhancement of or negative for antagonism of the SAA-induced response. See FIGS. 12 and 13 for maps of vectors used to construct a TLR2-HeLa-NF-κB reporter cell line In this method, any agent (e.g., small molecule, marcomolecule, protein, nonpeptide, etc.) that can reduce the SAA-induced NF-κB luciferase reporter is collected as a potential antagonist for SAA-induced TLR2 activation. In the second round of screening (described below), the HeLa cell line containing the reporter construct minues TLR2 is treated with the collected agents. If any of these agents also decrease TNF-alpha-induced NF-κB reporter expression, then the effect is deemed non-specific because it does not necessarily go through TLR2. Only the agents that specifically reduce SAA-stimulated, TLR2-mediated NF-κB reporter gene expression are considered antagonists of interest (i.e., candidate agents). This reporter-based screening method is highly sensitive, and can be used for high-throughput screening (HTS).

Figure 9:
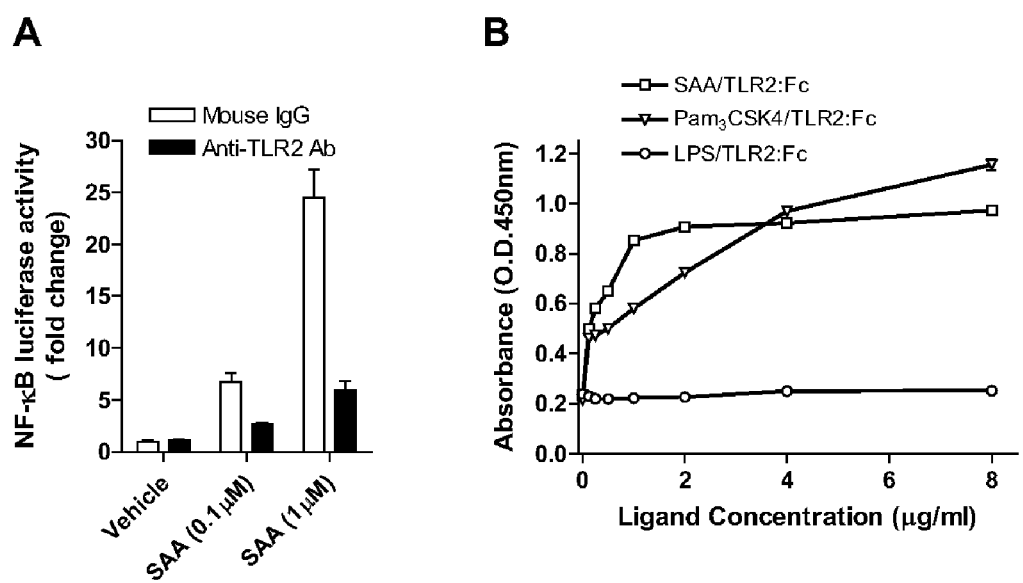
FIG. 9 is a series of graphs showing SAA interaction with TLR2. (A) Inhibition of SAA-induced NF-κB luciferase activity in TLR-HeLa cells by an anti-TLR2Ab. Isotype-matching IgG was used as a control. (B) SAA binding to TLR2 was measured in an ELISA-like assay using a TLR2 extracellular domain:Fc fragment fusion protein. Increasing concentrations of SAA, Pam3CSK4 and LPS (from 0.0625 to 8 μg/ml) were incubated with fixed amount (2 μg/ml) of the TLR2:Fc fusion protein. Binding was quantified using HRP-conjugated anti-mouse serum. Data shown are means of triplicate measurements from one of the three similar experiments.

Another example of a method for screening antagonists that disrupt the SAA/TLR2 interaction involves a binding assay that includes a TLR2 ectodomain (extracellular domain) fused to an Fc fragment of immunoglobulin (TLR2:Fc), such as the assay used in FIG. 9B. This assay is typically used as a follow-up or secondary assay to that assay described above. In other words, any compounds collected from the assay described above are subjected to the TLR2:Fc-based binding assay to confirm that the antagonistic effect is on the disruption of SAA-TLR2 binding. This method is generally carried out as follows and is also described in the Examples. A TLR2:Fc fusion protein is generated such that the N-terminal 588 amino acids of human TLR2 are fused in frame to the Fc portion of mouse IgG2a. The cDNA encoding for the resulting chimeric protein is cloned in pFuse-Fc vector (InvivoGen), and stably transfected into CHO cells. The fusion protein is purified from cell culture supernatant by standard protein A affinity chromatography and eluted with 0.1 mM glycine (pH2.2). High binding EIA/RIA plates (Corning) are coated with increasing concentrations of SAA, Pam3CSK4, or LPS from *E. coli* strain 0111:B4 overnight at 4° C. and blocked with 1% BSA in DPBS (Invitrogen) for 1 h, prior to incubation with 2 µg/ml of TLR2:Fc fusion protein for immunoadhesion. After 3 times wash with PBST (0.1% Tween-20 in DPBS), an HRP-labeled anti-mouse antibody (Calbiochem) is used for detection of captured TLR2:Fc. Absorbance at 450 nM is measured on a SpectraMax 340 plate reader (Molecular Devices).

Additionally, any SAA-stimulated, TLR2-mediated cellular response can be developed into a screening assay as described herein. For example, a SAA-induced MAP kinase phosphorylation assay can be used, in which TLR2-transfected and mock-transfected cell lines are compared. Mock-transfected cell lines are those cells transfected with an empty vector which is the same vector used for TLR2 transfection but does not contain the TLR2 cDNA.

The compositions described herein can be administered to subjects including human beings in any suitable formulation by any suitable method. For example, compositions including an agent that activates TLR2 (e.g., SAA protein or a nucleic acid encoding SAA protein) or a TLR2 antagonist may be directly introduced into a subject, including by intravenous (IV) injection, intraperitoneal (IP) injection, or in situ injection into target tissue (e.g., into the inflammatory joints in rheumatoid arthritis subjects, or into the GI tract of inflammatory bowel disease subjects). To improve patient compliance, a drug may be made orally effective. When used as a vaccine adjuvant, it will go with the vaccination method or route. For example, a conventional syringe and needle can be used to inject a composition including an agent that modulates TLR2 activation into a subject. Parenteral administration by injection can be performed, for example, by bolus injection or continuous infusion. Formulations of injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, compositions may be in powder form (e.g., lyophilized) for constitution with a suitable vehicle, for example, sterile pyrogen-free water, before use.

The compositions of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16$^{th}$ ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

In some embodiments, a composition including an immunologically effective amount of agent that activates TLR2 is administered to a subject to stimulate an immune response in the subject. An immunologically effective amount varies depending upon the health and physical condition of the subject to be treated, the taxonomic group of individual to be treated (e.g. human, nonhuman primate, etc.), the capacity of the subject's immune system to synthesize antibodies, the degree of protection desired, the formulation of the vaccine, the treating doctor's assessment of the medical situation, the condition to be treated or prevented, and other relevant factors. It is expected that the amount will fall in a relatively broad range that can be determined through routine trials.

EXAMPLES

Example 1

Identification of SAA as a Danger Signal Mediator for TLR2-Dependent G-CSF Production and Neutrophilia Increased neutrophil count or neutrophilia is a host response to bacterial infection as well as noninfectious insults such as trauma, malignancy and surgery. The mechanism by which noninfectious factors induce neutrophil expansion remains unknown. As described herein, the acute-phase protein SAA, a widely cited biomarker for inflammation, induces neutrophilia in mice. The SAA-induced neutrophilia is diminished in G-CSF deficient mice. In gain-of-function assays, SAA binds to the ectodomain of TLR2 and stimulates TLR2-mediated transcriptional activation, leading to increased expression of G-CSF. In TLR2 deficient mice, the SAA-induced G-CSF secretion and neutrophilia is significantly reduced. The ability of SAA to relay danger signal through TLR activation suggests a potential mechanism by which this acute-phase protein contributes to sterile inflammation.

Results

SAA induces G-CSF expression in monocytes and macrophages: To determine whether SAA plays a role in neutrophilia, the ability of SAA to stimulate G-CSF expression was investigated. Human peripheral blood monocytes (PBMC) were incubated with SAA, and the concentration of secreted G-CSF in the culture medium was determined at various time points after stimulation. The concentration of SAA used in this experiment (1 µM) was well within its physiological range (0.08 µM to 80 µM). As shown in FIG. 1A, SAA induced a robust production of G-CSF in PBMC that reached a level of 2,546 pg/ml/$10^6$ cells after 4 h of stimulation. At the end of the 24 h incubation, the G-CSF concentration in the culture medium reached to 7,340 pg/ml/$10^6$ cells. Since subsequent studies used mice for measurement of G-CSF secretion and neutrophilia, SAA-induced G-CSF expression in mouse bone marrow derived macrophages (BMDM) was determined, of which 98% were F4/80$^+$ CD14$^+$ based on flow cytometry analysis. FIG. 1B showed that BMDM responded to SAA with a significant increase in mouse G-CSF (encoded by the csf3 gene) secretion that reached a concentration of 155 pg/ml/$10^6$ cells after 8 h and 965 pg/ml/$10^6$ cells after 24 h. The basal level of G-CSF remained stable at approximately 42 pg/ml/$10^6$ cells over the entire course of incubation. Likewise, SAA stimulation of the mouse macrophage cell line RAW264.7 resulted in a time-dependent production of G-CSF (FIG. 1C).

It was next determined whether induction of G-CSF expression was a primary function of SAA or resulted from contaminating LPS in the SAA preparation. The LPS concentration in the recombinant SAA preparation was ≦0.1 ng/µg protein, translating into ≦1.14 ng/ml LPS in a typical experiment with 1 µM SAA. LPS at this or 10-fold higher concentrations was tested for its effect on the expression of G-CSF. As shown in FIG. 1D, LPS at 1 and 10 ng/ml did not induce G-CSF secretion in BMDM. At an LPS concentration of 100 ng/ml, a moderate increase in G-CSF secretion was observed. Therefore, the small amount of LPS found in the SAA preparation cannot account for the robust increase of G-CSF as seen in the above experiments. Given that most proteins are heat labile while LPS is heat resistant, the ability of heat-treated SAA (1 µM) and LPS (1 µg/ml) to stimulate G-CSF secretion in mouse BMDM was examined. After boiling for 25 min, LPS retained its ability to induce G-CSF production by ~83%. In contrast, the heat-treated SAA could no longer stimulate G-CSF secretion (FIG. 1E). In parallel experiments, polymyxin B, an amphiphilic cyclic polycationic peptide that specifically binds to LPS and blocks the cytokine-inducing effect of LPS (Stokes et al., 1989), was used to treat SAA or LPS prior to incubation with BMDM. Polymyxin B (50 µg/ml) had a minimal effect on the potency of SAA in stimulating G-CSF expression (FIG. 1E). Under the same experimental conditions, polymyxin B reduced LPS-stimulated G-CSF secretion by more than 70%. Collectively, these results confirmed that the observed induction of G-CSF secretion is a primary function of SAA.

Figure 2:
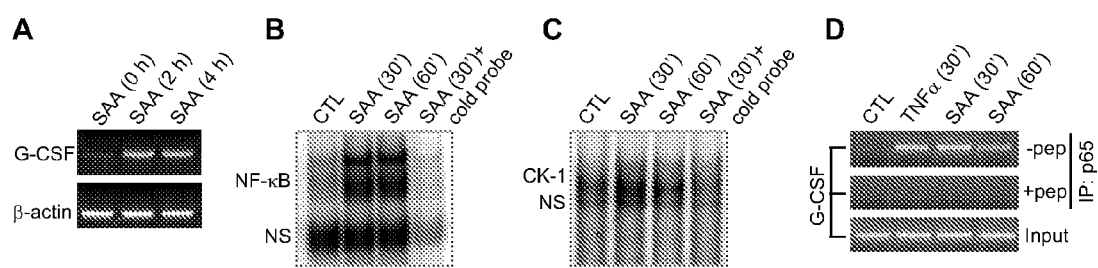
FIG. 2 is a series of photographs of gels showing SAA stimulation of NF-κB activation and G-CSF transcript accumulation. (A) RT-PCR detection of G-CSF transcript in SAA-stimulated mouse BMDM. β-actin was used as a PCR and sample loading control. (B) and (C) Electrophoretic mobility shift assays showing SAA-induced binding of NF-κB (B) and CK-1 (C) to the respective DNA sequence in the promoter region of G-CSF, using nuclear extracts prepared from SAA- or buffer (CTL) stimulated BMDM. (D) Chromatin immunoprecipitation assay was conducted with SAA or TNFα (50 ng/ml)-stimulated RAW264.7 cells. An anti-p65/RelA antibody was used together with or without a specific blocking peptide. The immunoprecipitated DNA was purified and amplified with PCR. DNA in total cell lysate was amplified with PCR and used as an input control.

To investigate the mechanism for SAA-induced G-CSF production, the level of G-CSF transcript in SAA-stimulated BMDM was determined. Elevation of G-CSF transcript level was observed after 2 h of SAA stimulation (FIG. 2A), a relatively fast response suggesting that SAA-induced G-CSF expression was not secondary to another cytokine. The induction of G-CSF transcript peaked at 4 h after SAA stimulation. Since transcription of the G-CSF gene involves NF-κB binding to the RelA/p65 consensus element in the CK-1 site of the G-CSF promoter (Dunn et al., 1994; Hareng and Hartung, 2002), the role of NF-κB in SAA-stimulated G-CSF expression was determined. Electrophoresis mobility shift assay (EMSA) showed that SAA stimulated the formation of NF-κB•DNA complex after 30 min, which was effectively competed off with unlabeled NF-κB probe (FIG. 2B). Using oligonucleotide probe based on the sequence of the CK-1 site (−161 to −152 in the G-CSF promoter), a protein •DNA complex (FIG. 2C) was identified. Finally, chromatin immunoprecipitation (ChIP) assay showed that a specific anti-RelA/p65 antibody was able to pull-down the CK-1 DNA fragment in cells treated with SAA or TNFα (50 ng/ml). Inclusion of a RelA/p65 antibody blocking peptide in the assay abrogated the immunoprecipitation (FIG. 2D). These results confirmed that SAA could stimulate binding of RelA/p65 to the CK-1 site.

Figure 3:
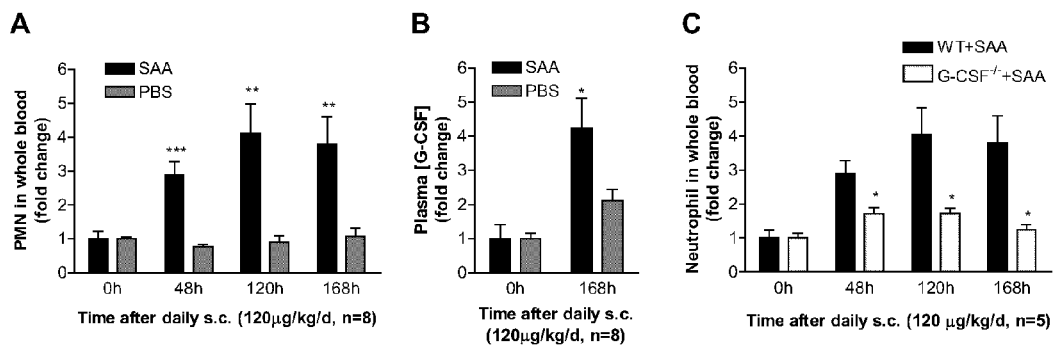
FIG. 3 is a series of graphs showing a correlation between SAA-induced G-CSF production and neutrophilia in mice. (A) SAA or PBS was injected subcutaneously into C57BL/6 mice (n=8) at a dose of 120 μg/kg in 0.2 ml of PBS at 24 h intervals. Blood samples were collected before (0 h) and 48, 120, and 168 h after the initial SAA injection. Neutrophil numbers in whole blood were determined with WBC differential counts and presented as fold changes. (B) The plasma concentration of G-CSF in SAA-injected mice was determined using ELISA at 0 h and 168 h after the initial administration as in A, and presented as fold changes (maximum 97 pg/ml). (C) SAA was injected subcutaneously into age- and sex-matched G-CSF$^{+/+}$ and G-CSF$^{-/-}$ mice (n=5), and peripheral blood neutrophil count was determined at the indicated time points as described in A above. *$P<0.05$, $P<0.005$, *$P<0.0005$, as compared to control mice.

SAA stimulates neutrophilia through G-CSF: To investigate whether SAA-induced G-CSF secretion contributes to neutrophilia, in vivo studies were conducted with daily administration of SAA in mice. C57BL/6 mice were injected subcutaneously (s.c.) with a daily dose of 120 µg SAA/kg body weight (~3 µg of SAA each mouse) for 7 consecutive days. At different time points after the injection was initiated, blood neutrophil numbers were determined and the results were compared to neutrophil numbers prior to SAA administration. Using PBS-injected mice as controls, daily injection of SAA was found to cause a significant rise of neutrophil numbers in peripheral blood starting at 48 h and continuing to the end of the 7-day period (FIG. 3A). The effectiveness of daily administration was demonstrated by a significantly elevated G-CSF level in the plasma at the end of the 7-day injection scheme (FIG. 3B), indicating that SAA could stimulate G-CSF production in vivo. To establish a causal relationship between SAA-induced G-CSF production and neutrophilia in mice, wild-type C57BL/6 mice wre compared with csf3$^{-/-}$ mice for changes in neutrophil count. As shown in FIG. 3C, csf3$^{-/-}$ mice exhibited a significantly reduced response to SAA based on peripheral blood neutrophil count at the end of 48, 120 and 168 h. These results support an important role of G-CSF in SAA-induced neutrophilia.

Figure 4:
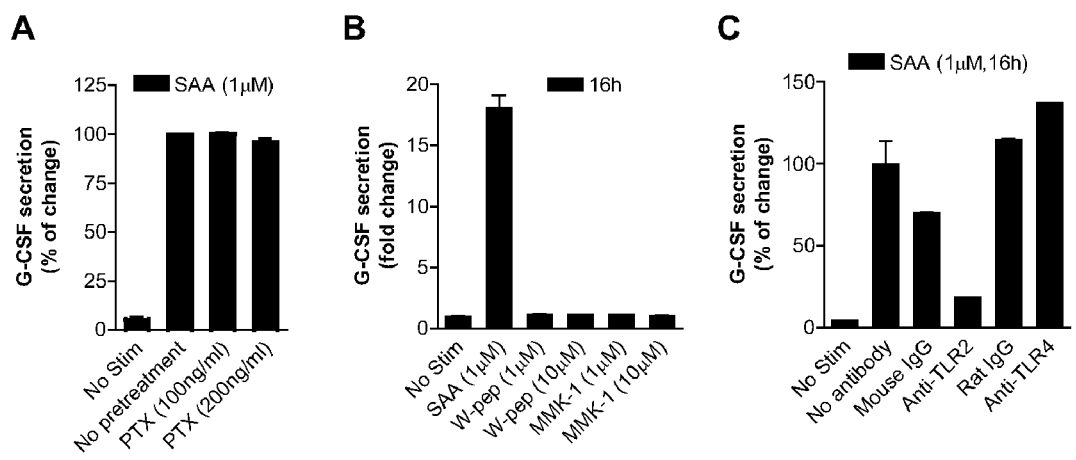
FIG. 4 is a series of graphs demonstrating identification of potential receptors for SAA-induced G-CSF expression. (A) Effect of pertussis toxin (PTX) on SAA-induced G-CSF secretion. Mouse BMDM were treated either with PTX at indicted concentrations or with buffer control overnight, and then stimulated with SAA for 16 h. The secreted G-CSF was determined with ELISA. (B) Mouse BMDM were stimulated with SAA, WKYMVm (W-pep), MMK-1 or buffer control, at indicated concentrations. After 16 h, secretion of G-CSF was determined with ELISA. (C) Inhibition of SAA-induced G-CSF secretion in mouse BMDM by an anti-TLR2 mouse Ab but not an anti-TLR4 rat Ab (functional grade, 5 μg/ml each). Antibody treatment of the cells was for 1 h. Isotype-matching IgG controls for the mouse and rat antibodies were included. Maximal G-CSF production in the above experiments was 446 pg/ml/$10^6$ cells.

TLR2 is a functional receptor of SAA for its induction of G-CSF expression: SAA has been shown to be a ligand for human formyl peptide receptor-like 1 (FPRL1) (Su et al., 1999), which is coupled to the G$\alpha$i proteins for transmembrane signaling. It was previously shown that FPRL1 is involved in SAA-induced IL-8 production in human neutrophils (He et al., 2003). It has also been shown that SAA binds to FPRL1 and stimulates the production of matrix metalloproteinase (O'Hara et al., 2004). In the experiments described herein, it was found that pretreatment of BMDM with pertussis toxin of up to 200 ng/ml, which ADP-ribosylates the Gi class of G$\alpha$ proteins (Bokoch et al., 1983) and blocks their interaction with G protein-coupled receptors such as FPRL1, produced no significant inhibition on SAA-induced G-CSF secretion (FIG. 4A). Moreover, FPRL1 agonists such as WKYMVm and MMK-1 were unable to stimulate G-CSF secretion in BMDM (FIG. 4B). These results suggest the presence of an SAA receptor that is different from FPRL1 and that mediates SAA-stimulated G-CSF secretion and neutrophilia. A role of TLR2 in SAA-stimulated G-CSF expression was examined. Functional grade antibodies against TLR2 and TLR4 were used to investigate the respective contributions of these receptors in SAA-induced G-CSF expression, and it was found that the anti-TLR2 antibody but not anti-TLR4 antibody caused marked reduction of G-CSF secretion (FIG. 4C). These results suggest TLR2 involvement in SAA-induced G-CSF secretion.

Figure 5:
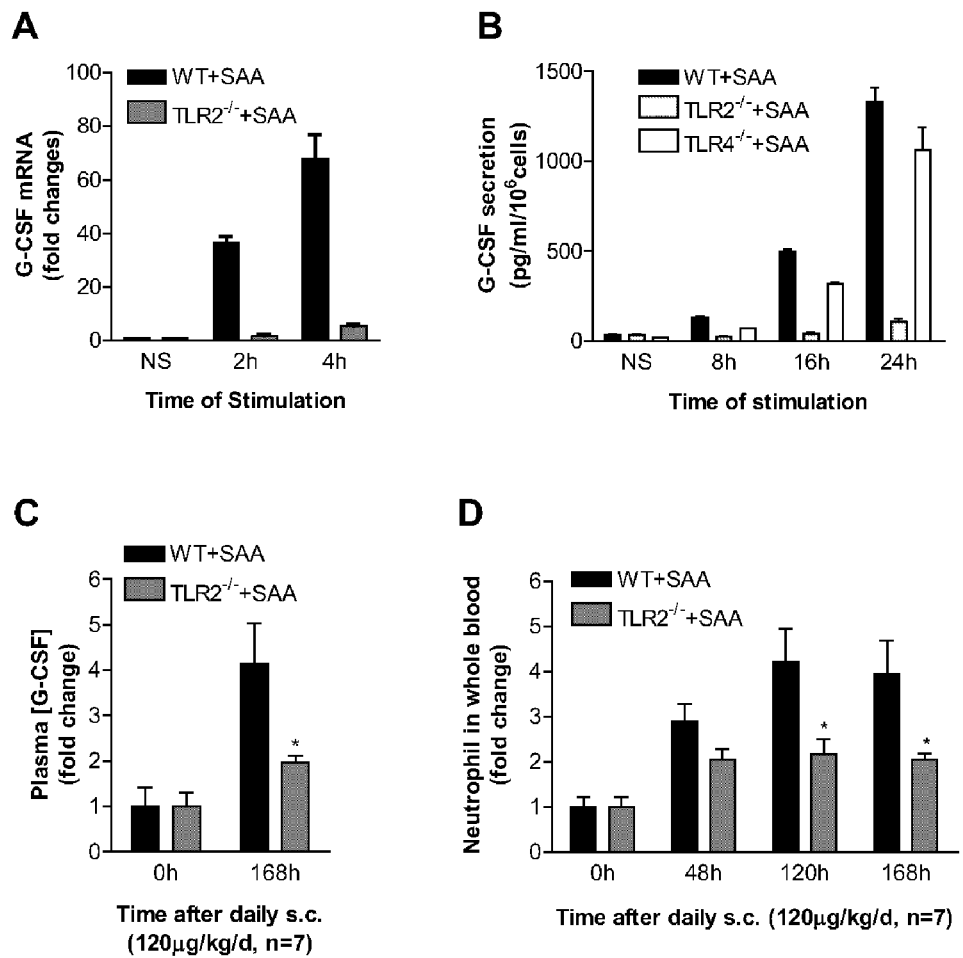
FIG. 5 is a series of graphs demonstrating a critical role of TLR2 in SAA-induced G-CSF secretion and neutrophilia. (A) The G-CSF mRNA level was determined by real-time PCR using RNA prepared from SAA (1 μM)-stimulated or unstimulated (NS) BMDM from wild-type C57BL/6 and tlr2$^{-/-}$ mice. The relative concentrations of the G-CSF transcript are presented as fold changes (means±SEM from four experiments, each in duplicate). (B) BMDM from wild-type C57BL/6 and tlr2$^{-/-}$ mice were similarly stimulated as in (A) and the secreted G-CSF was determine at the indicated time points using ELISA. (C) SAA was injected subcutaneously into age- and sex-matched C57BL/6 and TLR2$^{-/-}$ mice (n=7). The plasma concentration of G-CSF was determined at the end of the study (168 h). (D) SAA was injected into these mice as in (C). Blood samples were collected before injection (0 h) and at 48 h, 120 h, and 168 h after the initial injection. Neutrophil counts in the whole blood were obtained from WBC differential counts and presented as fold changes. *$P<0.05$ compared with wild-type mice.

TLR2 mediates the effect of SAA in G-CSF expression and neutrophila: To further determine a role of TLR2 in SAA-stimulated G-CSF expression and neutrophilia, wild-type and tlr2$^{-/-}$ BMDM were stimulated with SAA (1 μM) and the level of G-CSF transcript (FIG. 5A) was determined. SAA induced a 37-fold induction of the mouse G-CSF transcript within 2 h of stimulation. In comparison, a 2-fold induction over basal level was observed in tlr2$^{-/-}$ BMDM, representing a 94% reduction. Under similar experimental conditions, SAA stimulated increases in the transcripts of M-CSF (encoded by csf1; 11-fold over basal) IL-12p40 (33-fold) and IL-1 receptor antagonist (2.7-fold). In tlr2$^{-/-}$ BMDM, the SAA-stimulated induction of these transcripts was reduced by 84% (M-CSF), 86% (IL-12p40), and 80% (IL-1 receptor antagonist), respectively. Likewise, the ability of SAA to induce G-CSF protein secretion was drastically reduced (FIG. 5B). These results indicate that TLR2 is critical to the SAA-induced expression of G-CSF and selected cytokines. The effects of TLR2 gene deletion on SAA-induced G-CSF production and neutrophilia were determined in vivo. Subcutaneous injection of SAA was carried out in wild-type and tlr2$^{-/-}$ mice for up to 7 days. As shown in FIG. 5C, tlr2$^{-/-}$ mice produced significantly less G-CSF in the plasma than the wild-type mice. Consistent with this observation, the SAA-stimulated increase in peripheral blood neutrophils was significantly lower in tlr2$^{-/-}$ mice than in wild-type mice (FIG. 5D). These data support a role of TLR2 in mediating SAA-induced G-CSF production and neutrophilia.

Example 2

Identification of SAA as an Endogenous Ligand for TLR2

Results

Figure 6:
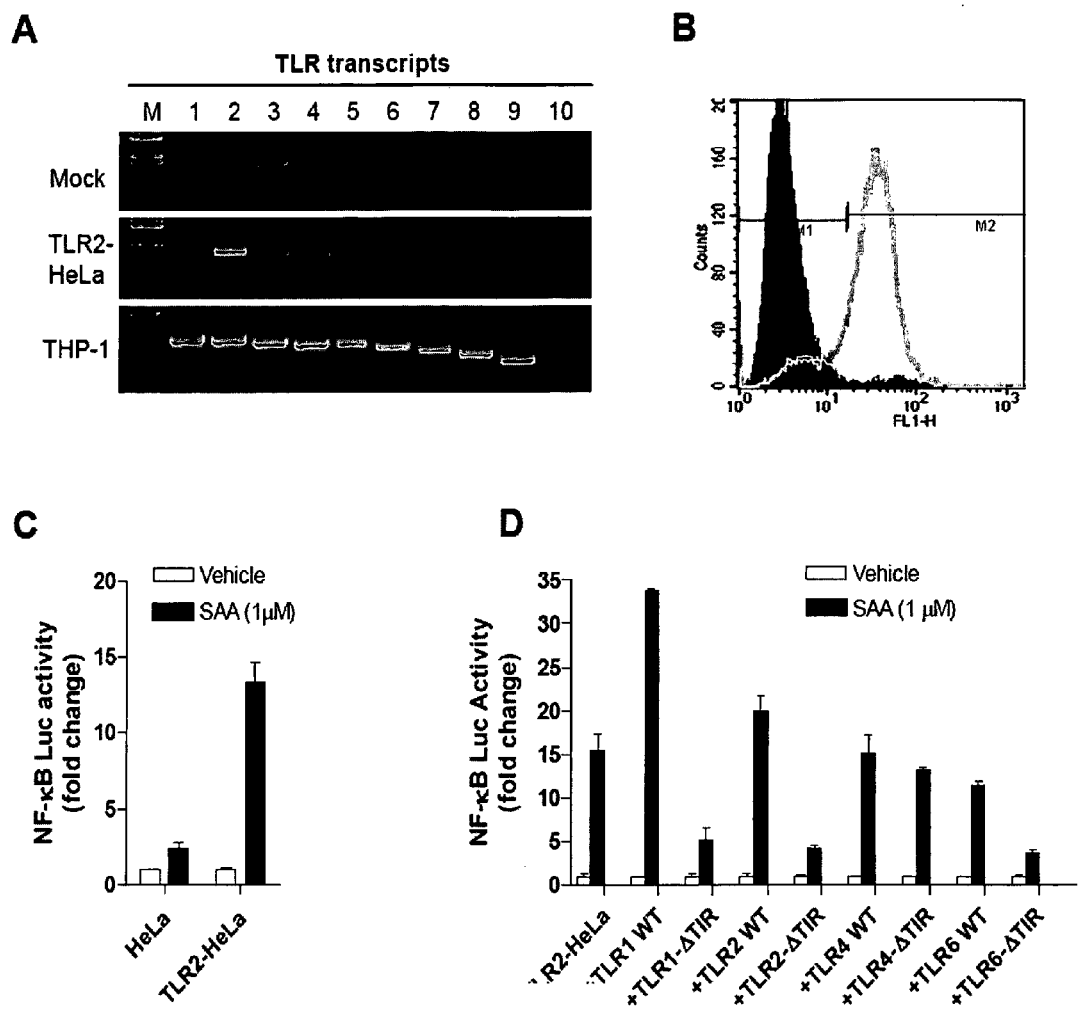
FIG. 6 is a photograph of a DNA gel, a histogram, and a pair of bar graphs demonstrating identification of TLR2 as a functional receptor of SAA. (A) RT-PCR analysis of TLR transcripts in mock-transfected and human TLR2-transfected HeLa cells, and in THP-1 cells (controls). Note that expression of TLR2 did not affect the level of other TLR transcripts. (B) Histogram showing expression of TLR2 on the surface of TLR2-transfected HeLa cells (open), compared to mock-transfected cells (filled), using an anti-TLR2 mAb and FITC-conjugated secondary Ab. (C) Enhanced NF-κB luciferase activity in TLR2-HeLa as compared to mock-transfected HeLa cells that were stimulated with SAA. (D) TLR1, TLR2, TLR4 and TLR6 were overexpressed in TLR2-HeLa cells. Also overexpressed were the ΔTIR domain mutants of these TLRs. The effects on SAA-induced NF-κB luciferase reporter activity were determined. Note that expression of TLR1 enhanced SAA-induced NF-κB activity, and expression of the ΔTIR domain mutants of TLR1, TLR2, and TLR6 reduced the SAA-induced NF-κB activity.

To determine whether TLR2 is a receptor for SAA, a TLR2-expressing cell line was prepared in HeLa cells, which contain very little endogenous TLR2 transcript (FIG. 6A, upper panel). Stable transfection of HeLa with a TLR2 expression construct (pUNO-hTLR2, FIG. 12) resulted in a substantial increase in the TLR2 transcript (FIG. 6A, middle panel), along with abundant cell surface expression of TLR2 as determined by flow cytometry (FIG. 6B). A significantly increased NF-κB luciferase activity (p<0.01) was detected in SAA-stimulated TLR2-HeLa cells compared to mock-transfected HeLa cells (FIG. 6C). TLR2 is a class I transmembrane protein that contains an extracellular ligand binding domain (ectodomain), a transmembrane domain and a cytoplasmic domain consisting of the Toll/IL-1/receptor/Resistance (TIR) motif. Studies have shown that TLR2 forms heterodimers with TLR1 and TLR6 (Ozinsky et al., 2000), which display different preference for TLR2 ligands (Hoebe et al., 2005; Takeuchi et al., 2002). The C-terminal TIR domain is conserved among TLRs and responsible for TLR signaling (O'Neill and Bowie, 2007; Takeda and Akira, 2004). To assess the relative contributions of TLRs to SAA signaling, TLR1, TLR2, TLR4 and TLR6 were overexpressed in the TLR2-HeLa cells, and their effects on SAA-induced NF-κB luciferase reporter activity were determined. As shown in FIG. 6D, exogenous expression of TLR1 but not TLR4 and TLR6 potentiated SAA-induced NF-κB luciferase activity, suggesting that TLR2 and TLR1 form a functional heterodimer for SAA signaling. In addition, the TIR domain deletion mutants (ΔTIR) of these receptors were expressed, which are negative regulators of TLR signaling. Expression of the ΔTIR mutants of TLR1, TLR2 and TLR6 caused significant inhibition (p<0.01) of SAA-induced NF-κB luciferase activity. The observed inhibitory effect of the TLR6-ΔTIR mutant may result from sequestration of the adaptor molecules (MyD88, TLRAP/MAL) interacting with TLR2, although the full-length TLR6 apparently did not potentiate SAA signaling. Expression of the ΔTIR mutant of TLR4 did not significantly affect SAA-induced NF-κB activation in TLR2-HeLa cells (FIG. 6D), suggesting the absence of TLR4 involvement in this assay.

Figure 7:
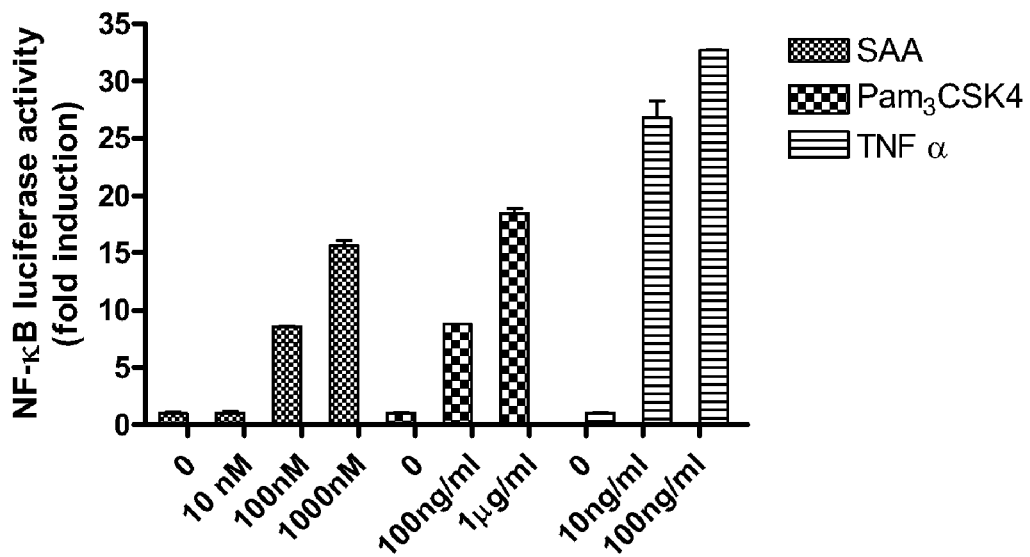
FIG. 7 is a series of studies showing SAA-induced response in transfected HeLa cells.
Figure 7:
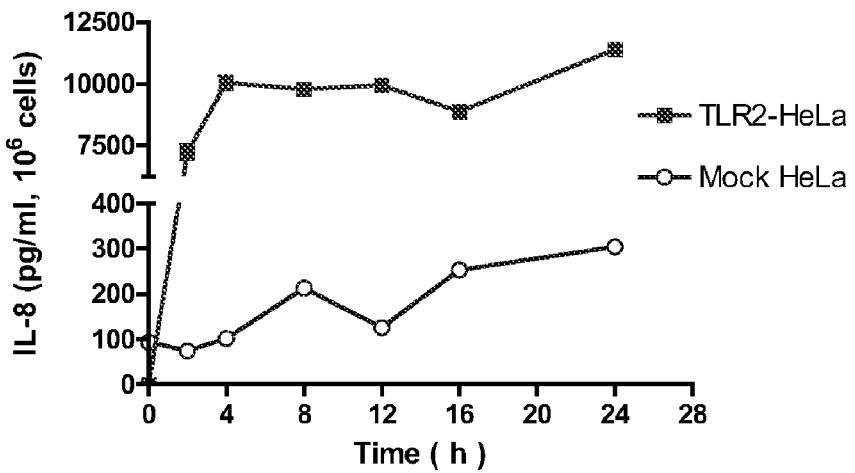

In addition to the TLR2-HeLa cell line, a HeLa cell line stably expressing TLR2 and a 5xNF-κB luciferase reporter (pNF-kappaB-Luc, FIG. 13) was generated. This second cell line offers improved consistency between experiments by eliminating the need for transiently transfecting the NF-κB reporter each time an reporter assay is conducted. The effectiveness of the TLR2-HeLa-NF-κB cell line has been demonstrated in reporter assays comparing SAA- and Pam3CSK4-induced luciferase activity (FIG. 7A). The TNFα-stimulated reporter activity was used as an independent indicator for comparison. Both cell lines have been and will be used in characterization of SAA-induced functions and in screening assays. Stimulation of the TLR2-HeLa cells with SAA (1 μM) caused a time-dependent increase in the secretion of IL-8, which was determined in the cell culture medium collected after the stimulation at given time points (FIG. 7B). The TLR2-independent effect in IL-8 secretion was determined in parallel, in mock-transfected HeLa cells lacking the exogenous TLR2 (FIG. 7B).

The ability of SAA to induce TLR2-dependent gene expression was evaluated using bone marrow derived mouse macrophages (FIG. 14). In this study, the cytokine gene expression profile in wild type and TLR2 knockout (TLR2-deficient) macrophages was compared. The SAA-induced expression of selected cytokine gene transcripts was determined using DNA microarray analysis and expressed as fold induction, in both the wild type and TLR2-deficient macrophages. The ratio of the expression (TLR2-deficient over wild type) was also calculated. The smaller the number in the ratio, expressed as percentage with 100% indicating no change, the larger the reduction in cytokine expression in the absence of TLR2 which reflects more dependency on TLR2.

Figure 8:
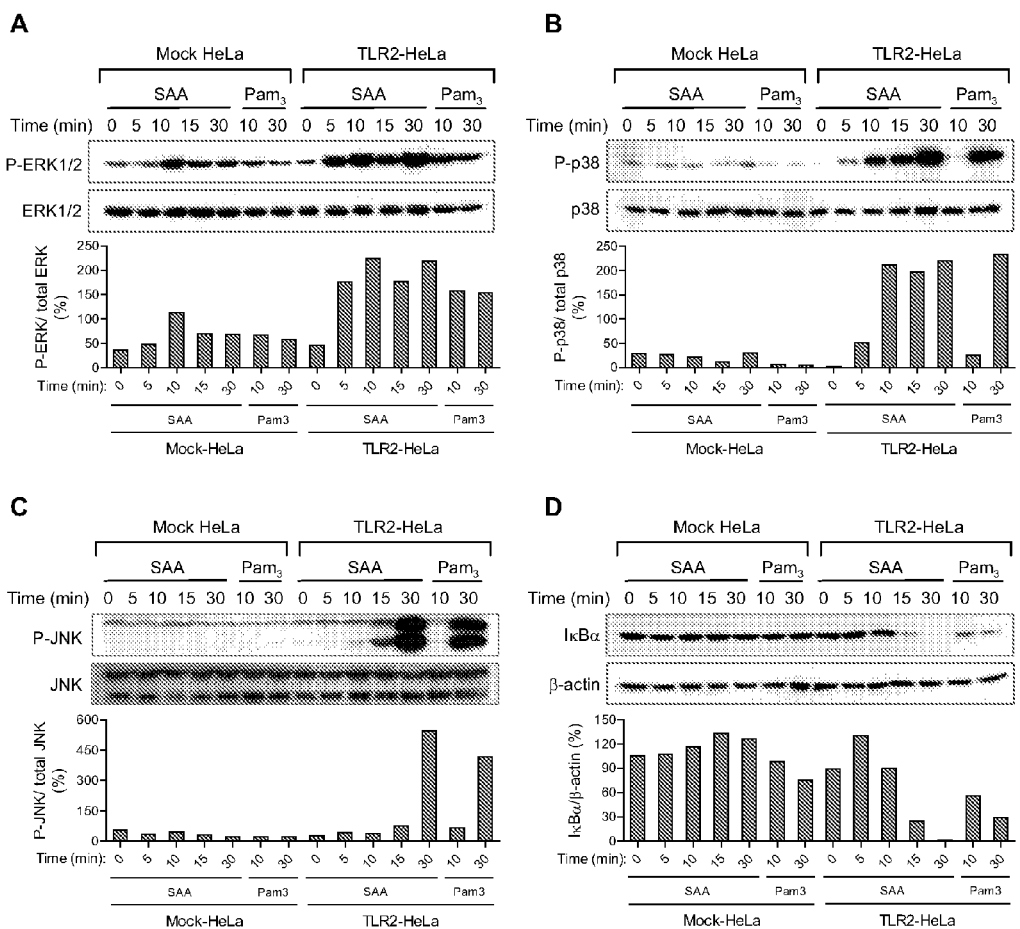
FIG. 8 is a series of protein gels and corresponding Western blotting graphs showing that SAA-induced TLR2-dependent signaling in transfected cells. Serum-starved TLR2-HeLa and mock-transfected HeLa cells were stimulated with SAA (1 μM) or Pam3CSK4 (1 μg/ml) for the indicated time. The phosphorylation level of ERK1/2 (A), p38 (B) and JNK (C) was detected by Western blotting using antibodies recognizing the phosphorylated forms of the MAP kinases (blots). (D) The level of cytoplasmic IκBα was detected by Western blotting using an anti-IκBα antibody and the β-actin levels in the corresponding samples were shown as loading controls. The relative levels of phosphorylation and IκBα degradation were determined through quantification of the blots, and data are presented in bar charts as the ratio of phosphorylated species to the unphosphorylated kinases, or IκBα level over the β-actin level. A representative set of data, from 3 repeating experiments, is presented.

SAA also induced robust phosphorylation of the MAP kinases ERK1/2, p38 and JNK in TLR2-HeLa cells, as compared to mock-transfected cells that displayed little phosphorylation of p38 and JNK (FIG. 8A-C). In mock-transfected cells, SAA but not Pam3CSK4 also induced ERK1/2 phosphorylation at 10 min, which could be mediated through an endogenous SAA receptor such as the scavenger receptor SR-BI (Baranova et al., 2005; Cai et al., 2005).

Also observed in TLR2-HeLa cells was a SAA-stimulated IκBα degradation, which normally leads to NF-κB activation. No IκBα degradation was observed in mock-transfected HeLa cells after SAA stimulation (FIG. 8D).

Figure 10:
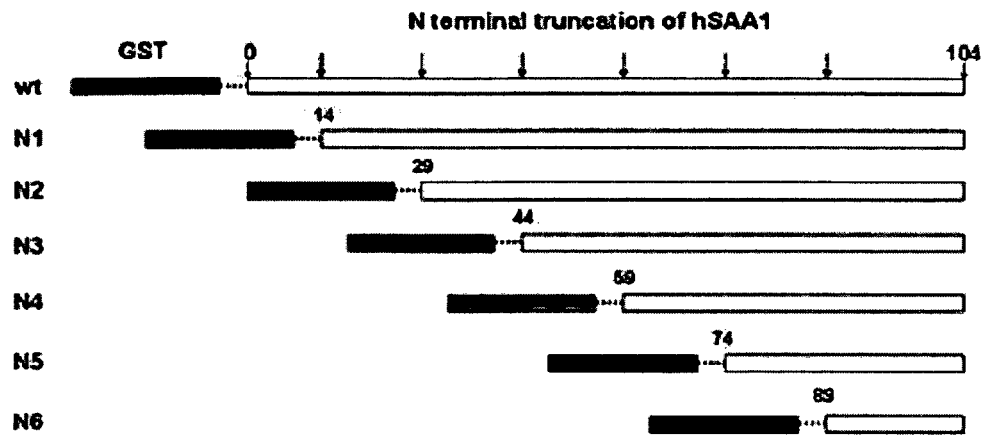
FIG. 10 is a schematic representation of SAA deletions made (A) and the effects of these deletions on SAA-induced NF-κB activation in TLR2-HeLa cells cotransfected with TLR1 (B). The effects of N-terminal deletion on SAA-induced, TLR2-dependent NF-κB luciferase reporter activity (B) were determined using full-length SAA (FL) and its progressive deletion mutants (N1-N6) fused to the C-terminus of glutathione S-transferase (A). The truncated SAA expressed with equal efficiency as the full-length SAA (data not shown). The same amount (~1 μM) of the SAA fusion protein was added to each sample. Results shown are means±SEM from 2 experiments, each performed in triplicate.
Figure 10:
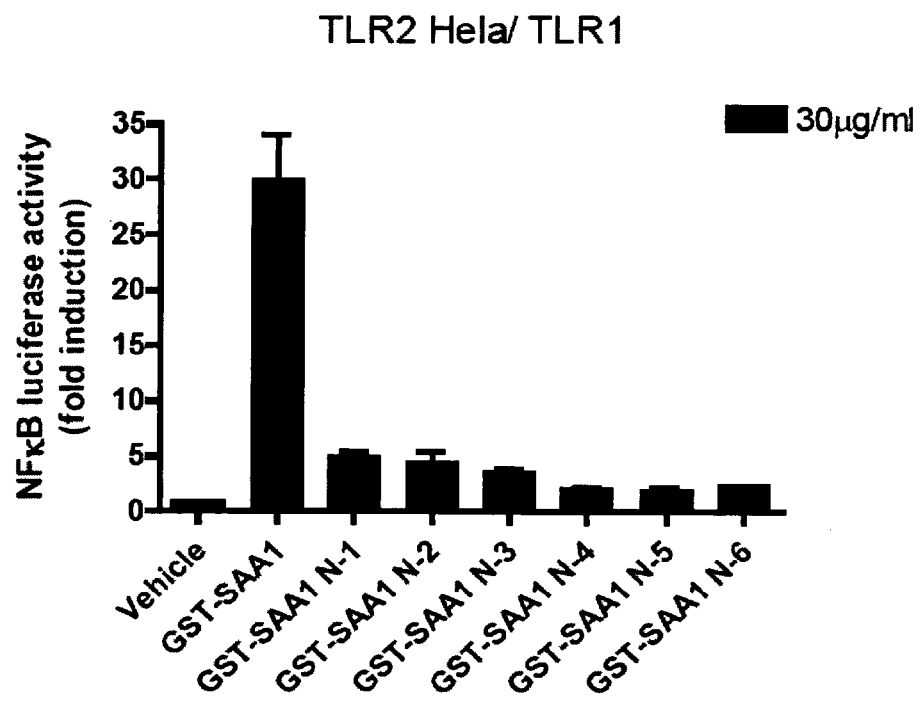

The above results support a role of TLR2 in SAA signaling. Whether SAA binds to TLR2 was then investigated. When the TLR2-HeLa cells were incubated with a neutralizing antibody against TLR2, significantly reduced NF-κB activation was observed (p<0.01, FIG. 9A). The specificity of SAA interaction with TLR2 was demonstrated in a binding assay using a TLR2 ectodomain fused to the Fc fragment of immunoglobulin (TLR2:Fc). A dose-dependent increase in SAA binding was observed (FIG. 9B). In contrast, LPS showed no significant binding to the TLR2:Fc fusion protein. To identify the structural determinant for SAA interaction with TLR2, progressive deletions were made from the N-terminus of SAA and the resulting proteins were examined in NF-κB luciferase reporter assay using TLR2-HeLa cells. As shown in FIG. 10, removal of as few as 14 amino acids from the N-terminus, a region conserved among acute-phase SAA proteins in humans and mice (Lowell et al., 1986; Uhlar and Whitehead, 1999), drastically reduced the ability of the resulting SAA to stimulate NF-κB activation through TLR2.

Figure 11:
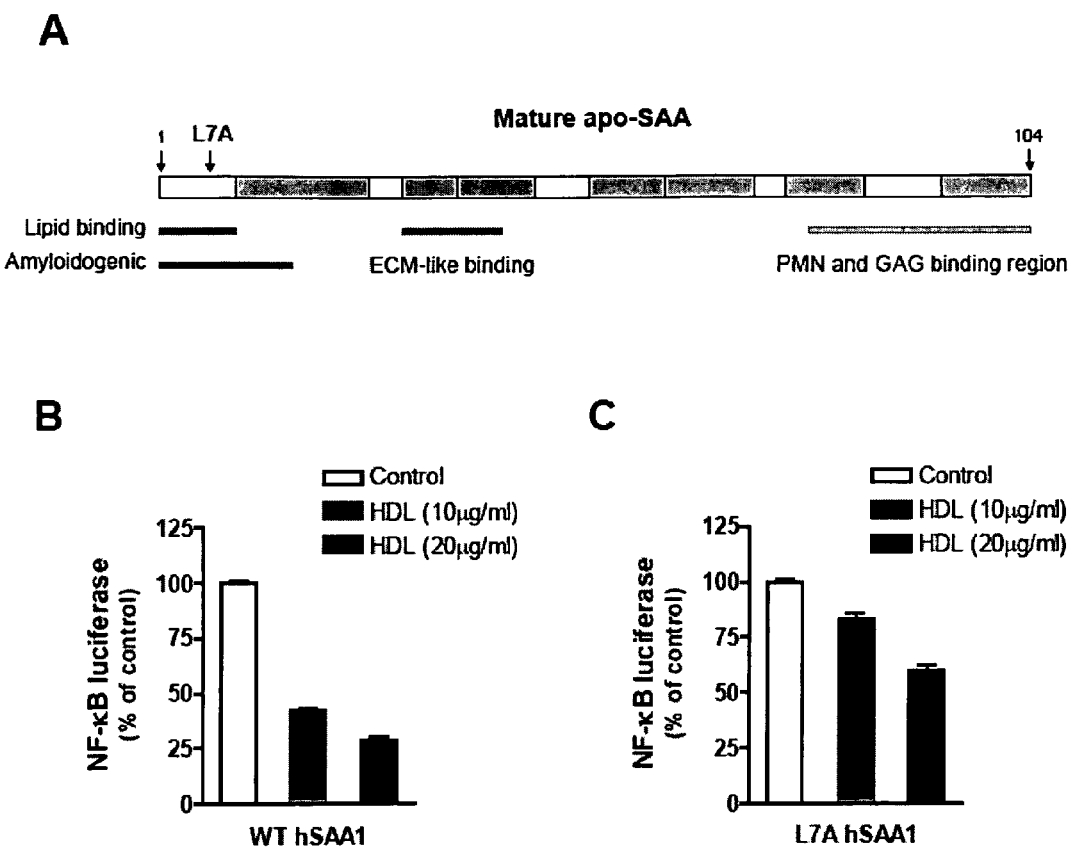
FIG. 11 is a schematic illustration of the structural domains of SAA (A), the effect of high-density lipoprotein (HDL) on SAA-induced NF-κB activation (B), and the effect of HDL on the NF-κB activation induced by the L7A mutation (Leucine to Alanine switch at position 7) of SAA. In these experiments, HDL was used at two different concentrations for preincubation with SAA. This treatment reduced SAA-stimulated NF-κB activation. The L7A mutation partially reversed the reduction effect by HDL.

The N-terminal domain of SAA is known for its interaction with HDL. The effect of HDL interaction on SAA-induced NF-κB activation was determined. FIG. 11 shows a schematic illustration of the structural domains of SAA (FIG. 11A), the effect of high-density lipoprotein (HDL) on SAA-induced NF-κB activation (FIG. 11B), and the effect of HDL on the NF-κB activation induced by the L7A mutation (Leucine to Alanine at position 7) of SAA (FIG. 11C). In these experiments, HDL was used at two different concentrations for preincubation with SAA. This treatment reduced SAA-stimulated NF-κB activation. The L7A mutation partially reversed the reduction effect by HDL.

Discussion

Results from the studies described herein demonstrate that SAA is a potent, endogenous mediator that stimulates G-CSF expression in isolated macrophages and in mice. These findings provide, for the first time, an explanation to the phenomenon that elevated level of acute-phase SAA is positively correlated with a contemporaneous neutrophilia. Neutrophils provide first-line host defense against bacterial and fungal infection. These terminally-differentiated myeloid cells possess highly specialized bactericidal functions including phagocytosis and generation of reactive oxygen species (Nauseef, 2007). Approximately 60% of the resources in bone marrow are committed to generating neutrophils which, upon release to blood circulation, have a lifespan of only 8-10 hours. Therefore, continual production of neutrophils is critical to innate immunity against invading bacteria and fungi. Because trauma, burn and surgery may lead to infection, an increase in neutrophil count in response to these noninfectious insults may be an evolutionarily conserved mechanism which prepares the host for possible insult by infectious agents. SAA apparently fills this important function by acting as an endogenous mediator of danger signal. Consistent with this notion, a study using sterile surgical procedure to induce nonspecific acute-phase response resulted in an increased G-CSF production and enhanced host resistance to bacterial infection (Noursadeghi et al., 2002). SAA expression is induced with primary cytokines (IL-6, IL-1β) and with LPS (Uhlar and Whitehead, 1999) and SAA, therefore, can enhance innate immune responses to pathogens through its ability to stimulate inflammatory cytokine expression and neutrophil expansion.

In the studies described herein, LPS contamination was addressed. First, it was shown that LPS, when used at concentrations 10-fold higher than those found in the SAA preparation, could not induce G-CSF expression in BMDM (FIG. 1D). Second, whereas LPS at higher concentrations (e.g., 100 ng/ml and above) induced G-CSF secretion, this effect was mostly heat-resistant while the SAA-induced G-CSF expression was heat-labile (FIG. 1E). Third, polymyxin B effectively eliminated the G-CSF-inducing capability of LPS but did not significantly reduce SAA-induced G-CSF expression (FIG. 1E). Fourth, functional grade anti-TLR2 antibody reduced SAA-stimulated G-CSF secretion, while a functional grade anti-TLR4 antibody had no inhibitory effect (FIG. 4C). Fifth, in TLR2-HeLa cells, overexpression of TLR4 did not further increase SAA-induced NF-κB activation, and overexpression of the ΔTIR mutant of TLR4 did not significantly alter the ability of SAA to stimulate NF-κB luciferase reporter expression (FIG. 6D). Sixth, SAA was found to directly bind to the ectodomain similar to Pam3CSK4. In contrast, no LPS binding to the TLR2 fusion protein was observed (FIG. 9B). Lastly, deletion mutagenesis studies described herein led to the identification of an N-terminal fragment of SAA as being important for its function through TLR2. The fact that all GST-fusion proteins except the full-length SAA-fused protein lacked the NF-κB activating capability strongly suggests a structural basis for TLR2 interaction, arguing against the notion that minute contaminants caused the potent induction of G-CSF expression as observed in this study.

The findings described herein that SAA induces neutrophilia through TLR2-mediated G-CSF production corroborates several recent reports demonstrating that SAA stimulates neutrophils and monocytes to secrete proinflammatory cytokines, matrix metalloproteinases, and monocyte tissue factor. This activity of SAA may be important in the maintenance of innate immunity and, in pathological conditions, prolong the inflammatory response. Sustained signaling through TLRs can trigger chronic inflammatory diseases without an identifiable cause of infection. Therefore, SAA-stimulated TLR2 activation may be linked to inflammatory and autoimmune diseases such as rheumatoid arthritis, atherosclerosis and Crohn' disease, in which elevated SAA has been documented (Chambers et al., 1987; Fyfe et al., 1997;

Malle and De Beer, 1996; O'Hara et al., 2000). Taking rheumatoid arthritis as an example, local production of SAA by macrophages and synoviocytes can exacerbate disease progression through increased neutrophil infiltration and neutrophil production of tissue degrading enzymes. The biochemical property of SAA and its low level of expression in normal tissues qualifies it as a damage-associated molecular pattern which, when recognized by the host, can initiate tissue-controlled immune response.

The ability of SAA to activate the IL-23/IL-17 pathway can also affect the progression of autoimmune and inflammatory diseases. A T cell-derived cytokine that regulates innate immunity, L-17 stimulates the production of proinflammatory cytokines such as IL-6 and IL-8, recruits neutrophils to site of inflammation, and contributes to the development arthritis, inflammatory bowel disease and experimental autoimmune encephalitis in animal models. Elevated SAA concentration was also found in atherosclerotic plaque (Meek et al., 1994). Given that TLR2 is a major pattern recognition receptor and is recently implicated in the development of atherosclerosis (Mullick et al., 2005), the findings described herein of SAA as an endogenous mediator for danger signal suggests that SAA production in atherosclerotic plaque may contribute to atherogenesis through persistent activation of TLR2.

In summary, the results described herein establish a link between increased production of SAA and G-CSF-mediated neutrophilia in mice. The results also identified TLR2 as a receptor that mediates the cytokine-inducing effect of SAA. These results provide direct evidence for a novel function of SAA in inflammation and immunity, demonstrating that the widely used biomarker for inflammatory diseases is not just a byproduct of inflammation but plays an active role in the regulation of inflammation and innate immunity.

Methods

Reagents: Recombinant human SAA was purchased from PeproTech Inc., (Rocky Hill, N.J., catalog no. 300-13). The endotoxin level is less than 0.1 ng/μg of protein. PMB and LPS, from *Escherichia coli* 0111:B4) were obtained from Sigma-Aldrich. Double-stranded consensus oligonucleotides for NF-κB were purchased from Promega and complementary oligonucleotides for the CK-1 site within the mouse G-CSF promoter region (mGcsf3-166: 5'-AGGAACA-GAGATTCCCCGATTTCAC-3') (SEQ ID NO:1) were custom synthesized and purified. The peptide MMK-1 (LESI-FRSLLFRVM (SEQ ID NO:2); >90% purity) was synthesized and purified by Macromolecular Resources (Fort Collins, Colo.) and W-peptide (WKYMVm) was obtained from Sigma-Aldrich. Pertussis toxin was purchased from Calbiochem. Anti-p65 antibody was obtained from Santa Cruz Biotechnology. Functional grade anti-TLR2, anti-TLR4 antibodies and their isotype control IgG were from eBioscience. All ELISA kits were purchased from Invitrogen. The *Limulus Amebocyte* Lysate kit (LAL QCL-1000) was obtained from Cambrex.

Plasmid Constructs: For deletion mutagenesis, DNA fragments coding for full-length human SAA1 (amino acid residues 1-104), SAA1 N-1 (15-104), SAA1 N-2 (30-104), SAA1 N-3 (45-104), SAA1 N-4 (60-104), SAA1 N-5 (75-104) and SAA1 N-6 (90-104) were PCR-amplified from a cloned cDNA encoding human SAA1, and ligated into the pGEX 4T-1 vector (Amersham Pharmacia). DNA fragments encoding human TLR1, TLR2, TLR4 and TLR6 without cytoplasmic domain (ΔTIR) were generated by PCR and cloned into the pUNO vector (InvivoGen). All constructs were verified by DNA sequencing.

Knockout mice: Heterozygote G-CSF (csf3$^{-/+}$) and G-CSF knockout mice in the genetic background B6/129P2 were purchased from Jackson Laboratory (stock number: 002398) and bred in-house. Genotyping was performed by PCR of tail genomic DNA according to manufacturer provided oligonucleotide sequence and procedures. Age and sex-matched littermates were used in experiments. TLR2 knockout mice (tlr2$^{-/-}$) were obtained from Jackson Laboratory (B6.129-Tlr2$^{tm1Kir}$/J, stock number 004650). The strain is maintained as a homozygote, and bred in house. Because this strain has been backcrossed to C57BL/6J for 9 generations, C57BL/6 mice, also purchased from Jackson Laboratory, were used as wild-type control (WT). All procedures involving mice were carried out using protocols approved by the Animal Care Committee at the University of Illinois at Chicago.

Figure 12:
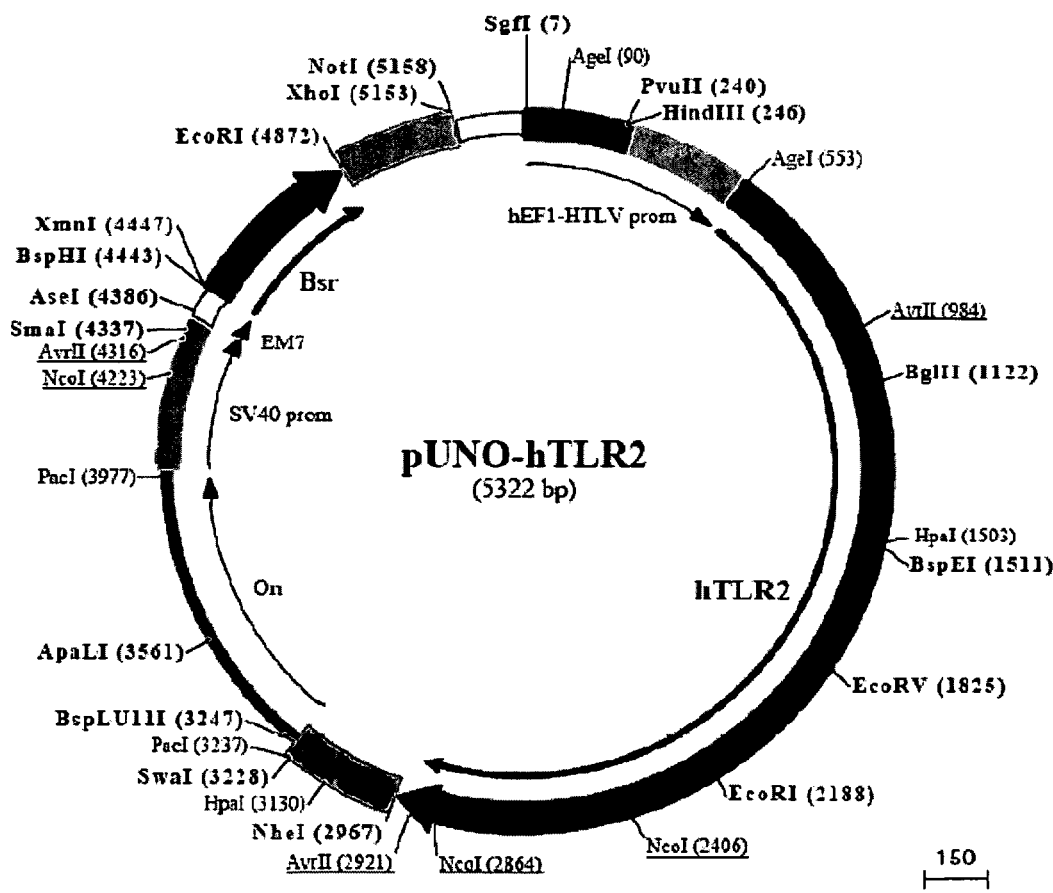
FIG. 12 is a map of vector pUNO-hTLR2.
Figure 13:
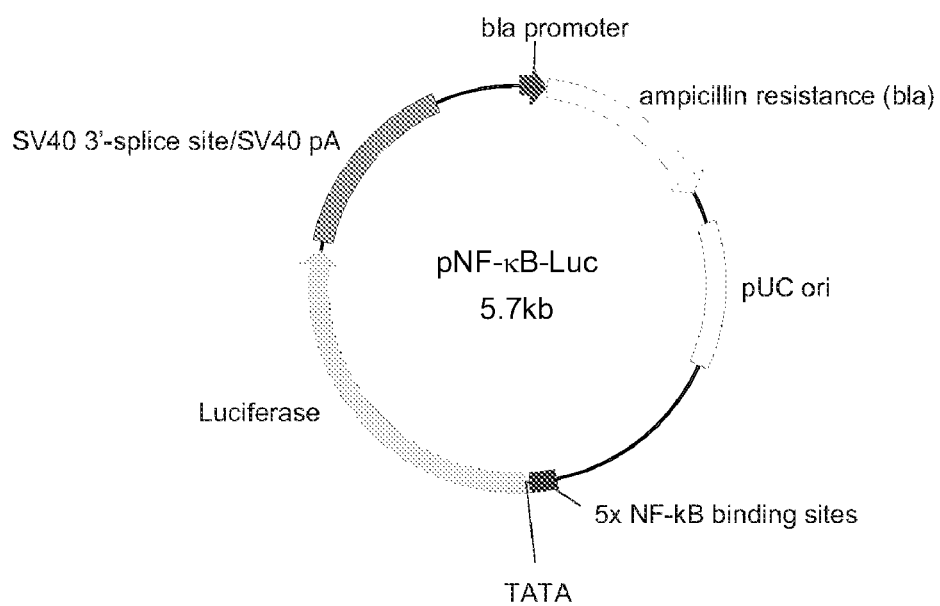
FIG. 13 is a map of vector pNF-κB-Luc.

Cell preparation and culture: Human peripheral blood monocytes were prepared from fresh, heparinized venous blood by Ficoll-Hypaque density-gradient centrifugation. Blood drawing followed a protocol approved by the Institutional Review Board at the University of Illinois at Chicago. Purified monocytes (>93% CD14$^+$ by flow cytometry) were kept in nonadherent condition in RPMI 1640 containing 0.5% FBS and maintained at 37° C. Mouse macrophages were differentiated from bone marrow cells. Mouse bone marrow cells were aspirated from the femurs of 8-12-week-old mice and cultured at 37° C. in 5% $CO_2$ in RPMI 1640 medium containing 10% FBS, 15% L-cell conditional medium, 10 mM HEPES, 2 mM L-glutamine, 100 IU/ml penicillin, and 50 μg/ml streptomycin. The medium was changed every three days. Macrophages (about 98% F4/80+ by flow cytometry) were obtained after 7 days of culture. The mouse macrophage cell line RAW264.7 cells were maintained in DMEM medium supplemented with 10% FBS, 10 mM HEPES, 2 mM L-glutamine, 100 IU/ml penicillin, and 50 μg/ml streptomycin. TLR2-HeLa cells were generated by transfection of HeLa cell with the expression construct pUNO-hTLR2 (InvivoGen). Stable transfectants were selected with Blasticidin at 20 μg/ml for 2 weeks. Mock-transfected HeLa cells were generated similarly, with a pUNO empty vector. Cells were maintained in DMEM supplemented with 10% heat-inactivated FBS, 2 mM L-glutamine, 100 IU/ml penicillin, and 50 μg/ml streptomycin. Expression of TLR2 was confirmed using an anti-TLR2 antibody (eBioscience) and FTTC-conjugated anti-mouse antibody, on a FACSCalibur flow cytometer (Becton Dickinson). FIGS. 12 and 13 are plasmid maps of pUNO-hTLR2 and pNF-κB-Luc, respectively.

Measurement of G-CSF expression: To measure the secreted G-CSF from human monocytes and mouse macrophages in vitro, cells were placed in serum-free DMEM medium and stimulated with the indicated ligands. Cell-free supernatants were collected by centrifugation at 1,000×g for 30 sec and assayed for human or mouse G-CSF using ELISA. Human PBMC were used as 2×10$^6$ cells/ml/sample, and mouse BMDM were seeded at 10$^6$ cells/ml and used as 0.5 ml/sample. To measure mouse plasma G-CSF, blood samples were collected and centrifuged at 1,000-2,000×g for 10 min at 4° C. Plasma samples were appropriately diluted and then checked for G-CSF concentration using ELISA. To measure mouse G-CSF transcripts, mouse DMEM (10$^6$ cells/ml, 5 ml/sample) were stimulated with 1 μM SAA for different periods of time. Total RNA was isolated with an RNeasy isolation kit (Qiagen) and cDNA was prepared with Superscript reverse transcriptase (Invitrogen). PCR amplification of G-CSF transcripts was accomplished with specific primers (F346: 5'-GAAGGCTTCCCTGAGTGGCT-3' (SEQ ID NO:3) and R980: 5'-CAGGGCTCACTGATTT TTTGG-3') (SEQ ID NO:4), generating a 634-bp fragment. M-actin gene (a 469 bp fragment) was used for verification of equal loading and of RT-PCR efficiency. Real-time quantitative PCR was performed on a ABI PRISM 7000 Sequence Detection System (Applied Biosystems) as described previously (He et al., 2006). All data were analyzed with the ABI PRISM 7000 SDS software (version 1.1). Relative level of mRNA for G-CSF was determined by normalizing with β-actin mRNA level. The sequences of the primers used are: F229 (5'-GGAG-CAAGTGAGGAAGATCCAG-3') (SEQ ID NO:5) and R502 (5'-ATCCAGCTGAAGCAAGTCCAAG-3') (SEQ ID NO:6) for G-CSF and F413 (5'-CCCTAAGGCCAACCGTGAA-3') (SEQ ID NO:7) and R882 (5'-CCAAGAAGGAAGGCTG-GAAAA-3') (SEQ ID NO:8) for β-actin.

EMSA: Nuclear extracts were isolated using the method of Dignam et al (Dignam et al., 1983) with minor modifications. For each sample, $5 \times 10^6$ cells were used. Radiolabeling of the NF-κB probe and CK-1 probe, binding reactions, electrophoresis, and autoradiography were conducted as described previously (He et al., 2003).

ChIP assay: Reagents were obtained from Upstate Biotechnology, and ChIP assay was performed as per manufacturers specifications with minor modifications. Briefly, a total of $1 \times 10^7$ RAW264.7 cells were harvested and resuspended in a serum-free DMEM medium absence or presence of 1 μM SAA, or 50 ng/ml of TNFα, and incubated for 30 or 60 min at 37° C. Following stimulation, cells were crosslinked and then washed and resuspended in SDS-lysis buffer, and were sonicated (4 times for 10 s each, with a setting at '4' on a Fisher Sonic 60 dismembrenator). Following centrifugation at 4° C. for 10 min, supernatants were diluted 1:10 with dilution buffer and were pre-cleared with salmon sperm DNA-saturated Protein A beads for 30 minutes. Immunoprecipitation was performed by adding 3 μg of polyclonal p65 specific antibody to the cell lysate overnight at 4° C. Specificity of interaction was verified via peptide competition for the antibody using a commercially available blocking peptide (72 μg) obtained from Santa Cruz Biotechnology. Immune complexes were precipitated by the addition of 50 μl of salmon sperm DNA-saturated Protein A and were washed with low salt buffer, high-salt buffer, LiCl buffer, and Tris-EDTA. The complex was extracted with elution buffer and the formaldehyde cross-linking was reversed by heat. The samples were then treated with proteinase K and purified using a PCR purification kit (Qiagen). Input control DNA was prepared as well. PCR was then performed on the purified DNA. The primers used were F-346: 5'-AGCAGTCTTGATCTGAG-CACCCAT-3'(SEQ ID NO:9) and R26: 5'-CTTCTGC-CAGGGCCCAGCTC-3' (SEQ ID NO:10), which cover the region of murine csf3 gene promoter from −346 to +26 nucleotide that contains the CK-1 element. The PCR products were analyzed on a 2.5% agarose gel.

NF-κB luciferase report assay.

Methods for the generation of TLR2-HeLa stable cell line: HeLa cells stably transfected with human TLR2 gene were generated by transfecting HeLa cells with the expression construct pUNO-hTLR2 (InvivoGen, San Diego, Calif.; GenBank accession number for human TLR2 cDNA is NM_003264) and selected with Blasticidin at concentration of 20 μg/ml for 2 weeks. The control HeLa cells were generated at the same time by transfecting with empty pUNO vector. Cells were maintained in DMEM supplemented with 10% heat-inactivated FB S, 2 mM L-glutamine, 100 IU/ml penicillin, and 50 μg/ml streptomycin. Expression of TLR2 was confirmed using an anti-TLR2 antibody (eBioscience) and FTTC-conjugated anti-mouse antibody, on a FACSCalibur flow cytometer (Becton Dickinson). The TLR2-HeLa and control cells were then co-transfected with 5xNF-κB reporter plasmids (pNF-κB-Luc, Stratagene, Cedar Creek, Tex., catalog no. 219077) and empty SFFV vector bearing a neomycin resistant gene. The TLR2-HeLa/NF-κB reporting cells were obtained after selecting with G418 at concentration of 400 mg/ml for 2-3 weeks. Cells ($5'10^5$/ml) were grown in DMEM supplemented with 10% heat-inactivated FBS, 2 mM L-glutamine, 100 IU/ml penicillin, and 50 mg/ml streptomycin.

Methods for using HeLa cells in reporter assay: Mock-transfected HeLa and TLR2-HeLa cells were maintained at ~$5 \times 10^5$ cells/well in six-well plates, transfected with plasmid expression vectors coding for a 3×κB-directed luciferase reporter, pCMVβ vector DNA (Promega) and/or other expression constructs as indicated. Total DNA concentration was adjusted to 1 μg/sample by addition of empty vector DNA. Transient transfection was performed using LipofectAmine Plus reagent (Invitrogen). Twenty-four hours after transfection, cells were serum-starved for 16-18 h, washed twice with PBS, and assayed with or without agonist stimulation. All luciferase assays were performed with duplicate or triplicate samples, and 2-4 independent experiments were usually conducted. Normalized data were plotted using the Prism software (version 4.0, GraphPad).

Assays for SAA-TLR2 interaction: The TL2:Fc fusion protein was generated such that the N-terminal 588 amino acids of human TLR2 protein were fused in frame with the Fc portion of mouse IgG2a. The cDNA encoding for the resulting chimeric protein was cloned in pFuse-Fc vector (InvivoGen), and transfected stably into CHO cells. The fusion protein was purified from cell culture supernatant by standard protein A affinity chromatography and eluted with 0.1 mM glycine (pH2.2). High binding EIA/RIA plates (Corning) were coated with increasing concentrations of SAA (PeproTech), Pam$_3$CSK4 (InvivoGen), or LPS from E. coli strain 0111:B4 (Sigma-Aldrich) overnight at 4° C. and blocked with 1% BSA in DPBS (Invitrogen) for 1 h, prior to incubation with 2 μg/ml of TLR2:Fc fusion protein for immunoadhesion. After 3 times wash with PBST (0.1% Tween-20 in DPBS), an HRP-labeled anti-mouse antibody (Calbiochem) was used for detection of captured TLR2:Fc with the appropriate chromogenic substrates (Invitrogen). Absorbance at 450 nM was measured on a SpectraMax 340 plate reader (Molecular Devices). Each experiment was performed in triplicate.

SAA-induced neutrophilia: For analysis of SAA-induced neutrophil increase, SAA was injected subcutaneously into both G-CSF deficient (csf3$^{-/-}$) (n=5) and csf3$^{+/+}$ (n=5), age- and sex-matched littermates (8-9 weeks, male), at doses of 120 μg/kg/d in 200 μl PBS. SAA was administered daily for 7 consecutive days (168 h). Blood samples were collected before and at 48, 120, and 168 h after the initial SAA injection. Age and sex-matched mice of both tlr2$^{-/-}$ (n=7) and C57BL/6 (n=7) were also used for this experiment. Blood was collected by eye puncture using heparinized capillaries and placed into EDTA-treated tubes. Total white blood cell (WBC) count and WBC differential count were determined using a Hemavet 950FS multispecies hematology analyzer (Drew Scientific).

Statistical analysis: Data analysis was carried out using paired Student t-test, with P values less than 0.05 considered statistically significant. The Prism software was used for statistical analysis (version 4.0, GraphPad).

Example 3

Additional Embodiments

In one embodiment of the present disclosure, a method includes providing a composition including the expression of TLR2 with another TLR (e.g., TLR1) that is known to form a heterodimer with TLR2. The composition can increase activation of transcription factor in the plurality of cells after SAA stimulation.

In one embodiment of the present disclosure, a method includes: providing a plurality of cells, each cell including a purified nucleic acid encoding TLR2; contacting the plurality of cells with SAA; analyzing changes in the phosphorylation pattern of signaling proteins including members of the MAP kinase family as an indication of cell activation; analyzing changes in the intracellular level of proteins including IκBα as indication of signaling events leading to transcriptional activation such as NF-κB activation.

In one embodiment of the present disclosure, a method includes providing a composition including the expression of a TIR domain deletion mutant of a TLR together with TLR2. The composition can decrease activation of transcription factor in the plurality of cells after SAA stimulation.

In one embodiment of the present disclosure, a method includes providing an interaction of a molecule with SAA, and such an interaction causes an alteration of the SAA-induced, TLR2-dependent bioactivity such as NF-κB activity. The molecule includes high density lipoprotein (HDL), and mutation of Leucin-7 which is known to be critical to HDL binding partially alleviates this inhibition. The molecule can be a small molecule, a macromolecule (e.g., antibody), a peptide, and a nonpeptide, wherein a small molecule, a macromolecule (e.g., antibody), a peptide, and a nonpeptide can be naturally occurring or synthetic.

In one embodiment of the present disclosure, a method includes providing a composition including fusion of the ectodomain of TLR2 to the Fc fragment of immunoglobulin for the measurement of the interaction of SAA with the ectodomain of TLR2.

In one embodiment of the present disclosure, a method includes providing a composition including SAA fusion protein with GST including deletion of portions of SAA for the measurement of the biological activity of SAA.

These are but a few examples of modifications that can be applied to the present disclosure without departing from the scope of the claims. Accordingly, the reader is directed to the claims section for a fuller understanding of the breadth and scope of the present disclosure.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Upon reviewing the aforementioned embodiments, it would be evident to an artisan with ordinary skill in the art that said embodiments can be modified, reduced, or enhanced without departing from the scope and spirit of the claims described below.

REFERENCES

Akira, S., and Sato, S. (2003). Toll-like receptors and their signaling mechanisms. Scand J Infect Dis 35, 555-562.

Baranova, I. N., Vishnyakova, T. G., Bocharov, A. V., Kurlander, R., Chen, Z., Kimelman, M. L., Remaley, A. T., Csako, G., Thomas, F., Eggerman, T. L., and Patterson, A. P. (2005). Serum amyloid A binding to CLA-1 (CD36 and LIMPII analogous-1) mediates serum amyloid A protein-induced activation of ERK1/2 and p38 mitogen-activated protein kinases. J Biol Chem 280, 8031-8040.

Bokoch, G. M., Katada, T., Northup, J. K., Hewlett, E. L., and Gilman, A. G. (1983). Identification of the predominant substrate for ADP-ribosylation by islet activating protein. J Biol Chem 258, 2072-2075.

Cai, L., de Beer, M. C., de Beer, F. C., and van der Westhuyzen, D. R. (2005). Serum amyloid A is a ligand for scavenger receptor class B type I and inhibits high density lipoprotein binding and selective lipid uptake. J Biol Chem 280, 2954-2961.

Chambers, R. E., MacFarlane, D. G., Whicher, J. T., and Dieppe, P. A. (1983). Serum amyloid-A protein concentration in rheumatoid arthritis and its role in monitoring disease activity. Ann Rheum Dis 42, 665-667.

Chambers, R. E., Stross, P., Barry, R. E., and Whicher, J. T. (1987). Serum amyloid A protein compared with C-reactive protein, alpha 1-antichymotrypsin and alpha 1-acid glycoprotein as a monitor of inflammatory bowel disease. Eur J Clin Invest 17, 460-467.

Demetri, G. D., and Griffin, J. D. (1991). Granulocyte colony-stimulating factor and its receptor. Blood 78, 2791-2808.

Dignam, J. D., Lebovitz, R. M., and Roeder, R. G. (1983). Accurate transcription initiation by RNA polymerase II in a soluble extract from isolated mammalian nuclei. Nucleic Acids Res 11, 1475-1489.

Dunn, S. M., Coles, L. S., Lang, R. K., Gerondakis, S., Vadas, M. A., and Shannon, M. F. (1994). Requirement for nuclear factor (NF)-kappa B p65 and NF-interleukin-6 binding elements in the tumor necrosis factor response region of the granulocyte colony-stimulating factor promoter. Blood 83, 2469-2479.

Furlaneto, C. J., and Campa, A. (2000). A novel function of serum amyloid A: a potent stimulus for the release of tumor necrosis factor-alpha, interleukin-1beta, and interleukin-8 by human blood neutrophil. Biochem Biophys Res Commun 268, 405-408.

Fyfe, A. I., Rothenberg, L. S., DeBeer, F. C., Cantor, R. M., Rotter, J. I., and Lusis, A. J. (1997). Association between serum amyloid A proteins and coronary artery disease: evidence from two distinct arteriosclerotic processes. Circulation 96, 2914-2919.

Gabay, C., and Kushner, I. (1999). Acute-phase proteins and other systemic responses to inflammation. N Engl J Med 340, 448-454.

Hareng, L., and Hartung, T. (2002). Induction and regulation of endogenous granulocyte colony-stimulating factor formation. Biol Chem 383, 1501-1517.

He, R., Sang, H., and Ye, R. D. (2003). Serum amyloid A induces IL-8 secretion through a G protein-coupled receptor, FPRL1/LXA4R. Blood 101, 1572-1581.

He, R., Shepard, L. W., Chen, J., Pan, Z. K., and Ye, R. D. (2006). Serum amyloid A is an endogenous ligand that differentially induces IL-12 and IL-23. J Immunol 177, 4072-4079.

Hoebe, K., Georgel, P., Rutschmann, S., Du, X., Mudd, S., Crozat, K., Sovath, S., Shamel, L., Hartung, T., Zahringer, U., and Beutler, B. (2005). CD36 is a sensor of diacylglycerides. Nature 433, 523-527.

Kushner, I., and Rzewnicki, D. (1999). Acute phase response. In Inflammation: Basic principles and clinical correlates, J. I. Gallin, and R. Snyderman, eds. (Philadelphia, Lippincott Willams & Wilkins), pp. 317-329.

Lowell, C. A., Potter, D. A., Stearman, R. S., and Morrow, J. F. (1986). Structure of the murine serum amyloid A gene family. Gene conversion. J Biol Chem 261, 8442-8452.

Malle, E., and De Beer, F. C. (1996). Human serum amyloid A (SAA) protein: a prominent acute-phase reactant for clinical practice. Eur J Clin Invest 26, 427-435.

Medzhitov, R., and Janeway, C., Jr. (2000). The Toll receptor family and microbial recognition. Trends Microbiol 8, 452-456.

Meek, R. L., Urieli-Shoval, S., and Benditt, E. P. (1994). Expression of apolipoprotein serum amyloid A mRNA in human atherosclerotic lesions and cultured vascular cells: implications for serum amyloid A function. Proc Natl Acad Sci USA 91, 3186-3190.

Mullick, A. E., Tobias, P. S., and Curtiss, L. K. (2005). Modulation of atherosclerosis in mice by Toll-like receptor 2. J Clin Invest 115, 3149-3156.

Nauseef, W. M. (2007). How human neutrophils kill and degrade microbes: an integrated view. Immunol Rev 219, 88-102.

Noursadeghi, M., Bickerstaff, M. C., Herbert, J., Moyes, D., Cohen, J., and Pepys, M. B. (2002). Production of granulocyte colony-stimulating factor in the nonspecific acute phase response enhances host resistance to bacterial infection. J Immunol 169, 913-919.

O'Hara, R., Murphy, E. P., Whitehead, A. S., FitzGerald, O., and Bresnihan, B. (2000). Acute-phase serum amyloid A production by rheumatoid arthritis synovial tissue. Arthritis Res 2, 142-144.

O'Hara, R., Murphy, E. P., Whitehead, A. S., FitzGerald, O., and Bresnihan, B. (2004). Local expression of the serum amyloid A and formyl peptide receptor-like 1 genes in synovial tissue is associated with matrix metalloproteinase production in patients with inflammatory arthritis. Arthritis Rheum 50, 1788-1799.

O'Neill, L. A., and Bowie, A. G. (2007). The family of five: TIR-domain-containing adaptors in Toll-like receptor signalling. Nat Rev Immunol 7, 353-364.

Ozinsky, A., Underhill, D. M., Fontenot, J. D., Hajjar, A. M., Smith, K. D., Wilson, C. B., Schroeder, L., and Aderem, A. (2000). The repertoire for pattern recognition of pathogens by the innate immune system is defined by cooperation between toll-like receptors. Proc Natl Acad Sci USA 97, 13766-13771.

Patel, H., Fellowes, R., Coade, S., and Woo, P. (1998). Human serum amyloid A has cytokine-like properties. Scand J Immunol 48, 410-418.

Robertson, C. M., and Coopersmith, C. M. (2006). The systemic inflammatory response syndrome. Microbes Infect 8, 1382-1389.

Stokes, D. C., Shenep, J. L., Fishman, M., Hildner, W. K., Bysani, G. K., and Rufus, K. (1989). Polymyxin B prevents lipopolysaccharide-induced release of tumor necrosis factor-alpha from alveolar macrophages. J Infect Dis 160, 52-57.

Su, S. B., Gong, W., Gao, J. L., Shen, W., Murphy, P. M., Oppenheim, J. J., and Wang, J. M. (1999). A seven-transmembrane, G protein-coupled receptor, FPRL1, mediates the chemotactic activity of serum amyloid A for human phagocytic cells. J Exp Med 189, 395-402.

Takeda, K., and Akira, S. (2004). TLR signaling pathways. Semin Immunol 16, 3-9.

Takeuchi, O., Sato, S., Horiuchi, T., Hoshino, K., Takeda, K., Dong, Z., Modlin, R. L., and Akira, S. (2002). Cutting edge: role of Toll-like receptor 1 in mediating immune response to microbial lipoproteins. J Immunol 169, 10-14.

Uhlar, C. M., and Whitehead, A. S. (1999). Serum amyloid A, the major vertebrate acute-phase reactant. Eur J Biochem 265, 501-523.

Vallon, R., Freuler, F., Desta-Tsedu, N., Robeva, A., Dawson, J., Wenner, P., Engelhardt, P., Boes, L., Schnyder, J., Tschopp, C., et al. (2001). Serum amyloid A (apoSAA) expression is up-regulated in rheumatoid arthritis and induces transcription of matrix metalloproteinases. J Immunol 166, 2801-2807.

What is claimed is:

1. A method for identifying a TLR2 antagonist comprising:
   providing a composition comprising a candidate TLR2 antagonist;
   contacting a TLR2 polypeptide comprising a TLR2 extracellular domain with a serum amyloid A (SAA) polypeptide in the presence of the composition; and
   determining binding of the TLR2 polypeptide to the SAA polypeptide, wherein a disruption in binding of TLR2 to SAA compared to TLR2 binding to SAA in the absence of the composition indicates the composition is a TLR2 antagonist.

2. The method of claim 1, wherein the candidate TLR2 antagonist is selected from the group consisting of: a small molecule, a macromolecule, a peptide, and a nonpeptide, wherein the small molecule, macromolecule, peptide, and nonpeptide can be naturally occurring or synthetic.

3. The method of claim 1, wherein the composition further comprises a pharmaceutically acceptable carrier.

4. The method of claim 1, wherein the TLR2 polypeptide is expressed on the surface of a cell.

5. The method of claim 4, wherein the TLR2 polypeptide is expressed from a cDNA encoding full-length TLR2 expressed in the cell.

6. The method of claim 5, wherein the cell further comprises a nucleic acid encoding a plurality of NF-κB binding sites operably linked to at least one expression control sequence and a reporter gene.

7. The method of claim 6, wherein the reporter gene is luciferase.

8. The method of claim 6, wherein determining the binding of the recombinant TLR2 polypeptide to the SAA polypeptide is by detecting expression of the reporter gene.

9. The method of claim 5, wherein determining the binding of the recombinant TLR2 polypeptide to the SAA polypeptide is by detecting the expression of a SAA-inducible protein produced by the cell.

10. The method of claim 9, wherein a SAA-inducible protein produced by the cell is a proinflammatory cytokine in the cell.

11. The method of claim 10, wherein the cytokine is G-CSF.

12. The method of claim 1, wherein the recombinant polypeptide comprising a TLR2 extracellular domain is fused to an antibody Fc fragment.

13. The method of claim 12, wherein determining the binding of the recombinant TLR2 polypeptide to the SAA polypeptide is by ELISA assay.

14. The method of claim 2, wherein the candidate TLR2 antagonist is an antibody.

15. The method of claim 1, wherein the SAA polypeptide is a recombinant SAA polypeptide.

16. The method of claim 15, wherein the recombinant SAA polypeptide is fusion protein.

* * * * *

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial
<220> FEATURE:
<223> OTHER INFORMATION: oligonucleotide

<400> SEQUENCE: 1
aggaacagag attccccgat ttcac                                         25

<210> SEQ ID NO 2
<211> LENGTH: 13
<212> TYPE: PRT
<213> ORGANISM: ARTIFICIAL
<220> FEATURE:
```

```
<223> OTHER INFORMATION: SYNTHETIC PEPTIDE

<400> SEQUENCE: 2

Leu Glu Ser Ile Phe Arg Ser Leu Leu Phe Arg Val Met
1               5                   10

<210> SEQ ID NO 3
<211> LENGTH: 20
<212> TYPE: DNA
<213> ORGANISM: ARTIFICIAL
<220> FEATURE:
<223> OTHER INFORMATION: OLIGONUCLEOTIDE

<400> SEQUENCE: 3
gaaggcttcc ctgagtggct                                                 20

<210> SEQ ID NO 4
<211> LENGTH: 21
<212> TYPE: DNA
<213> ORGANISM: ARTIFICIAL
<220> FEATURE:
<223> OTHER INFORMATION: OLIGONUCLEOTIDE

<400> SEQUENCE: 4
cagggctcac tgattttttg g                                               21

<210> SEQ ID NO 5
<211> LENGTH: 22
<212> TYPE: DNA
<213> ORGANISM: ARTIFICIAL
<220> FEATURE:
<223> OTHER INFORMATION: OLIGONUCLEOTIDE

<400> SEQUENCE: 5
ggagcaagtg aggaagatcc ag                                              22

<210> SEQ ID NO 6
<211> LENGTH: 22
<212> TYPE: DNA
<213> ORGANISM: ARTIFICIAL
<220> FEATURE:
<223> OTHER INFORMATION: OLIGONUCLEOTIDE

<400> SEQUENCE: 6
atccagctga agcaagtcca ag                                              22

<210> SEQ ID NO 7
<211> LENGTH: 19
<212> TYPE: DNA
<213> ORGANISM: ARTIFICIAL
<220> FEATURE:
<223> OTHER INFORMATION: OLIGONUCLEOTIDE

<400> SEQUENCE: 7
ccctaaggcc aaccgtgaa                                                  19

<210> SEQ ID NO 8
<211> LENGTH: 21
<212> TYPE: DNA
<213> ORGANISM: ARTIFICIAL
<220> FEATURE:
<223> OTHER INFORMATION: OLIGONUCLEOTIDE

<400> SEQUENCE: 8
ccaagaagga aggctggaaa a                                               21
```

```
<210> SEQ ID NO 9
<211> LENGTH: 24
<212> TYPE: DNA
<213> ORGANISM: ARTIFICIAL
<220> FEATURE:
<223> OTHER INFORMATION: OLIGONUCLEOTIDE

<400> SEQUENCE: 9
agcagtcttg atctgagcac ccat                                       24

<210> SEQ ID NO 10
<211> LENGTH: 20
<212> TYPE: DNA
<213> ORGANISM: ARTIFICIAL
<220> FEATURE:
<223> OTHER INFORMATION: OLIGONUCLEOTIDE

<400> SEQUENCE: 10
cttctgccag ggcccagctc                                            20
```